United States Patent [19]

Christensen et al.

[11] 4,281,002
[45] Jul. 28, 1981

[54] 3-(2-AMINOETHYLTHIO)-6-AMIDO-7-OXO-1-AZABICYCLO(3.2.0)-HEPT-2-ENE-2-CARBOXYLIC ACID

[75] Inventors: Burton G. Christensen, Metuchen; Ravindra N. Guthikonda, Edison; David B. R. Johnston, Warren; Susan M. Schmitt, Scotch Plains, all of N.J.

[73] Assignee: Merck & Co., Inc., Rahway, N.J.

[21] Appl. No.: 81,518

[22] Filed: Oct. 3, 1979

Related U.S. Application Data

[62] Division of Ser. No. 30,786, Apr. 17, 1979, Pat. No. 4,224,336.

[51] Int. Cl.$^3$ .................. C07D 487/04; A61K 31/395
[52] U.S. Cl. ..................................... 424/263; 424/274; 260/245.2 R; 546/272
[58] Field of Search ............... 260/245.2 T, 245.2; 546/272; 424/263, 274

[56] References Cited

U.S. PATENT DOCUMENTS

| | | |
|---|---|---|
| 4,123,547 | 10/1978 | Christensen et al. ............... 424/274 |
| 4,150,145 | 4/1979 | Christensen et al. ............... 424/274 |
| 4,168,268 | 9/1979 | Datta et al. ....................... 195/80 R |
| 4,172,144 | 10/1979 | Bouffard et al. ................... 260/245.2 |

Primary Examiner—Alan L. Rotman
Attorney, Agent, or Firm—Hesna J. Pfeiffer; James A. Arno

[57] ABSTRACT

Disclosed are 3-(2-aminoethylthio)-6-amido-7-oxo-1-azabicyclo [3.2.0]hept-2-ene-2-carboxylic acids having the structure:

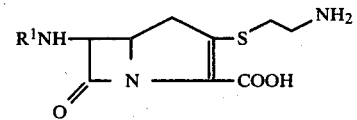

wherein R$^1$ is hydrogen or acyl. Such compounds as well as their pharmaceutically acceptable salt, ester and amide derivatives are useful as antibiotics. Also disclosed are processes for the preparation of such compounds, pharmaceutical compositions comprising such compounds and methods of treatment comprising administering such compounds and compositions when an antibiotic effect is indicated.

2 Claims, No Drawings

3-(2-AMINOETHYLTHIO)-6-AMIDO-7-OXO-1-AZABICYCLO(3.2.0)-HEPT-2-ENE-2-CARBOXYLIC ACID

This is a division of application Ser. No. 30,786, filed Apr. 17, 1979, now U.S. Pat. No. 4,224,336, issued Sept. 23, 1980.

BACKGROUND OF THE INVENTION

This invention relates to 3-(2-aminoethylthio)-6-amido-7-oxo- 1-azabicyclo[3.2.0]hept-2-ene-2-carboxylic acids and its pharmaceutically acceptable salt, ester and amide derivatives thereof which are useful as antibiotics and which may be represented by the following generic structural formula (I):

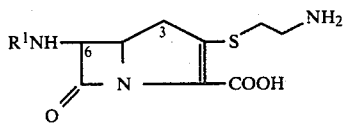

wherein $R^1$ is hydrogen and all acyl radicals known to be effective in the related, bicyclic β-lactam antibiotic art, e.g., the cephalosporins and penicillins. $R^1$ as acyl is defined representatively below.

This invention also relates to the carboxyl derivatives of I which are antibiotics and which may be represented by the following generic structure (I):

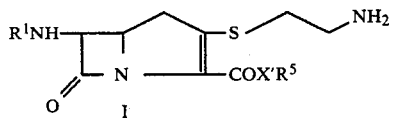

wherein X' is oxygen, sulphur or NR' (R'=H or lower alkyl having 1-6 carbon atoms); $R^5$ is, inter alia, representatively selected from the group consisting of hydrogen, conventional blocking groups such as trialkylsilyl, acyl and the pharmaceutically acceptable salt, ester and amide moieties known in the bicyclic β-lactam antibiotic art; the definition of $R^5$ is given in greater detail below; $R^1$ is, in addition to hydrogen, acyl. The term "acyl" is by definition inclusive of the alkanoyls including derivatives and analogues thereof such as thio analogues wherein the carbonyl oxygen is replaced by sulphur; as well as sulphur and phosphorous acyl analogues such as substituted sulfonyl-, sulfinyl-, and sulfenyl- radicals, and substituted P (III and V) radicals such as substituted phosphorous-, phosphoric-, phosphonous- and phosphonic- radicals, respectively. Such acyl radicals of the present invention are further defined below.

This invention also relates to processes for the preparation of such compounds (I); pharmaceutical compositions comprising such compounds; and to methods of treatment comprising administering such compounds and compositions when an antibiotic effect is indicated.

There is a continuing need for new antibiotics. For unfortunately, there is no static effectiveness of any given antibiotic because continued wide scale usage selectively gives rise to resistant strains of pathogens. In addition, the known antibiotics suffer from the disadvantage of being effective only against certain types of microorganisms. Accordingly the search for new antibiotics continues.

Thus, it is an object of the present invention to provide a novel class of antibiotics which are useful in animal and human therapy and in inanimate systems. These antibiotics are active against a broad range of pathogens which representatively include both gram positive bacteria such as *S. aureus, Strep. pyogenes,* and *B. subtilis* and gram negative bacteria such as *E. coli, Proteus morganii,* Serratia, Pseudomonas and Klebsiella. Further objects of this invention are to provide chemical processes for the preparation of such antibiotics and their non-toxic pharmaceutically acceptable salts; pharmaceutical compositions comprising such antibiotics; and to provide methods of treatment comprising administering such antibiotics and compositions when an antibiotic effect is indicated.

DETAILED DESCRIPTION OF THE INVENTION

The compounds of the present invention (I, above) are conveniently prepared by the following scheme:

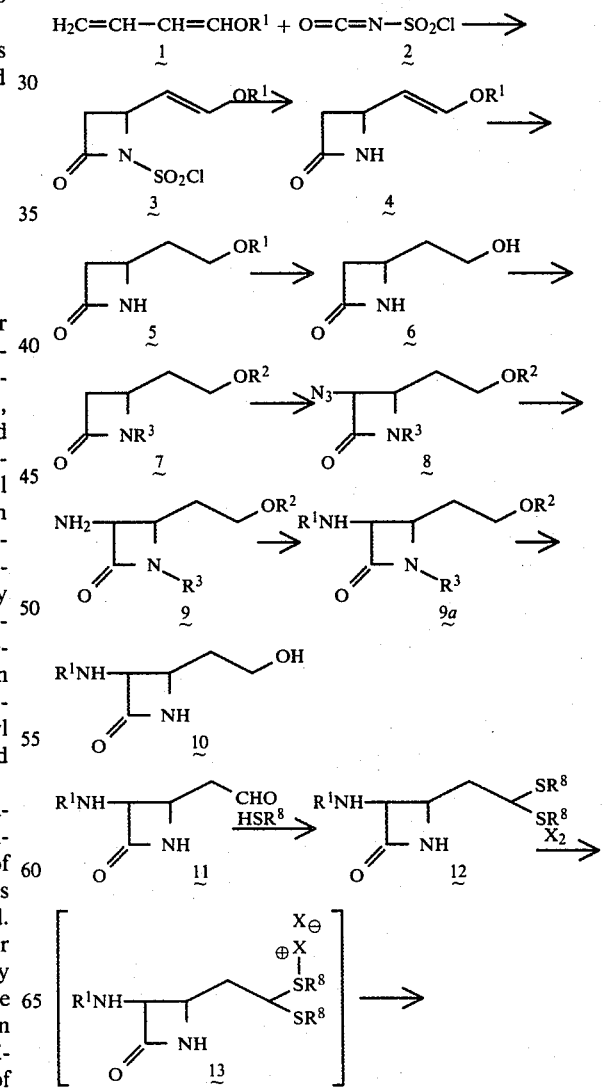

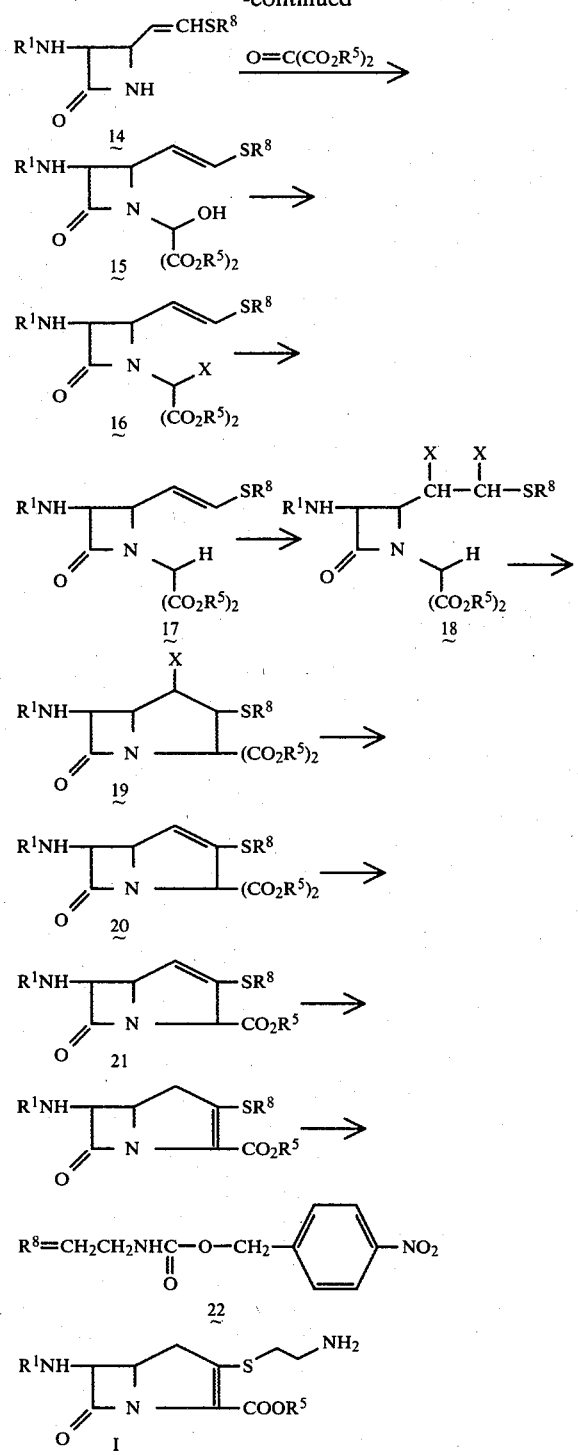

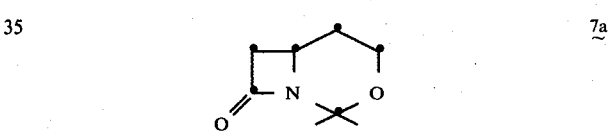

In words relative to the above diagram, the 4-(2-substituted-vinyl)azetidine-2-one, 4, starting material is prepared by reacting an R$^{1°}$-oxybutadiene, 1, with chlorosulfonylisocyanate 2. The reaction is conducted without solvent or may be run in solvent such as diethyl ether, ethyl acetate, chloroform, methylene chloride, or the like, at a temperature of from −78° C. to 25° C. for from a few minutes to 1 hour to provide 3. The radical R$^{1°}$ is an easily removable acyl blocking group such as an alkanoyl or aralkanoyl which bears no functional group or groups which might interfere with the desired course of reaction (1+2→3→4). Intermediate species 3 is converted to the sulfinamide by reductive hydrolysis to 4 at pH 6–8. Typically the reaction solution comprising 3 is contacted (5–30 minutes) with an aqueous solution (at 0°–25° C.) of a reducing agent such as sodium sulfite, thiophenol, or the like, at pH 6–8 to provide 4.

The reaction 4→5 is a reduction, and is preferably achieved by hydrogenation in a solvent such as ethyl acetate ether, dioxane, tetrahydrofuran (THF), ethanol or the like at 0° to 25° C. for from 5 mintues to 2 hours under 1 to 10 atmospheres of hydrogen in the presence of a hydrogenation catalyst such as a platinum metal or oxide thereof such as 10% Pd/C or the like.

The de-blocking reaction 5→6 is usually desirable when R$^{1°}$ is acyl to permit the establishment of preferred protecting groups R$^2$ and R$^3$. The preferred de-blocking procedure is by alcoholysis wherein the solvent is a lower alkanol such as methanol, ethanol or the like in the presence of the corresponding alkali metal alkoxide, such as sodium methoxide. Typically, the reaction is conducted for from 5 minutes to 1 hour at a temperature of from −10° to 25° C.

Blocking groups R$^3$ and R$^2$ are established (6→7) to provide a suitably protected species for introduce of the azide (7→8). There is no criticality in the choice of blocking groups, provided only that they do not interfere with the intended reaction. R$^3$ may be hydrogen, a triorganosilyl group such as trimethylsilyl or the like, or a cyclic ether such as 2-tetrahydropyranyl; R$^2$ may also be a cyclic ether such as 2-tetrahydropyranyl; alternatively R$^3$ and R$^2$ may be joined together to form protected species such as 7a:

For example, species such as 7a are conveniently prepared by treating 6 with 2,2-dimethoxypropane in the presence of a catalyst such as boron trifluoride etherate, toluene sulphonic acid, or the like in a solvent such a methylene chloride, ether, chloroform, dioxane or the like at a temperature of from −10° to 35° C. for from a few minutes to 1 hour.

The azide intermediate 8 is prepared by treating 7 in a solvent such as tetrahydrofuran (THF), dimethoxyethane, ether or the like with a base such as lithium diisopropylamide, n-butyl lithium, potassium hydride or the like at a temperature of from −78° to 0° C. for from 2 to 60 minutes; whereupon an azide reagent such as tosylazide is introduced; after 0.5 to 5 hours at −78° to 0° C., the mixture is treated with a disproportionating agent such as trimethylchlorosilane to provide the azide 8 which may be isolated.

The amino intermediate, 9, is obtained by treating 8 in a solvent such as ethylacetate, dioxane, ethanol, or the like in the presence of a platinum or palladium metal catalyst such as 10% Pd/C under a hydrogen pressure of from 1–4 atmospheres for from 1 to 24 hours at 0° to 25° C.

N-acylation of 9 provides 9a. The reaction 9→9a may be accomplished by any of a variety of well-known procedures such as treating 9, in a solvent such as methylene chloride, chloroform or the like with the acid chloride calculated to provide the acyl radical R$^1$ in the presence of from 1-5 equivalents of K$_2$HPO$_4$ in water or in the presence of pyridine at a temperature of from 0° to 25° C. for from 5-60 minutes.

The deblocking reaction $\underline{9a} \rightarrow \underline{10}$ is typically conducted by acid hydrolysis such as aqueous acetic acid at a temperature of from 25° C. to 75° C. for from 5 minutes to 3 hours.

The aldehyde intermediate $\underline{11}$ is prepared by treating $\underline{10}$ with an oxidizing agent such as CrO$_3$.2(pydridine) in CH$_3$CN, 1:1 mixture of dimethylsulfoxide and acetic anhydride, cyclohexylcarbodiimide in DMSO or the like at a temperature of from 0°-25° C. for from 5 minutes to 1 hour. The resulting species $\underline{11}$ in a solvent such as acetonitrile, mehylene chloride, chloroform or the like at a temperature of from −10 to 25° C. is treated with an excess of the reagent HSR$^8$ in the presence of an acid catalyst such as boron trifluoride etherate, toluene sulphonic acid or the like to provide $\underline{12}$. Typically, the reaction requires from 1 to 60 min. HSR$^8$ is HSCH$_2$CH$_2$NHR$^9$; wherein R$^9$ is a blocking group such as p-nitrobenzyloxycarbonyl, benzyloxycarbonyl, or the like. The preparation of HSR$^8$ is given below in the Examples.

The vinyl sulphide $\underline{14}$ is obtained via intermediate $\underline{13}$ by treating $\underline{12}$ wih a halogen such as chlorine or bromine (X=Cl or Br) in a solvent such as ether, methylene chloride, tetrahydrofuran, glyme or the like at a temperature of from −78° to 30° C. for from 1 to 30 minutes, followed immediately by treating with an olefin such as cyclohexene, isobutylene, or the like in the presence of base such as triethylamine, DBU, sodium hydride, or the like in a solvent such as DMF, glyme, THF, HMPA. The solution is held at −20° to 25° C. for from 1 to 8 hours to yield $\underline{14}$.

The vinyl sulphide species $\underline{14}$ is reacted with a diester of oxomalonic acid (or its monohydrate) to provide $\underline{15}$. There is no criticality as to the identity of the ester moiety, R$^5$, of the oxomalonic acid. R$^5$ may be a conventional, easily removable blocking group or it may be a pharmaceutically acceptable ester moiety. Suitable ester radicals R$^5$ are p-nitrobenzyl, benzyl, o-nitrobenzyl, t-butyl, 2,2,2-trichloroethyl. The reaction $\underline{14} \rightarrow \underline{15}$ is typically conducted in a high boiling organic solvent such as benzene, toluene, cyclohexane, halo aromatic or the like at a temperature of from about 50° C. to reflux for from 0.5 to 6 hours.

The halogenation reaction $\underline{15} \rightarrow \underline{16}$ is typically conducted in a solvent such as THF, glyme, ether, methylene chloride, chloroform or the like in the presence of a halogenating agent such as thionyl chloride, phosphorous pentachloride or the like in the presence of base such as pyridine at a temperature of from −20° to 25° C. for from 5 minutes to 3 hours. The selective reduction of $\underline{15} \rightarrow \underline{17}$ via $\underline{16}$ is completed by treating $\underline{16}$ with tributylphosphine, triphenylphosphine or the like in aqueous DMF or similar aqueous systems involving dioxane, THF, glyme, DMSO, or acetone at a temperature of from about 0°-50° C. for from 10 minutes to 5 hours.

Species $\underline{17}$ is halogenated by the previous procedure ($\underline{12} \rightarrow \underline{13}$), but omitting the addition of the cyclohexene or other olefin, to provide the dihalo species $\underline{18}$. Species $\underline{18}$ is treated with a base such as triethylamine, sodium hydride or potassium hydride in a solvent such as DMF, acetonitrile, methylene chloride, chloroform, glyme or the like at a temperature of from about −78° to 25° C. for 1 to 5 hours to provide $\underline{19}$. Species $\underline{19}$ is converted to $\underline{20}$ on treatment with a strong base such as 1,5-diazabicyclo[5.4.0]undec-5-ene(DBU), 1,5-diazabicyclo[3.4.0]non-5-ene(DBN), or the like in a solvent such as DMSO, acetone, chloroform, DMF THF, glyme or the like or on treatment with AgF in pyridine at a temperature of from 0°-40° C. for from ¼ to 24 hours. The reaction $\underline{20} \rightarrow \underline{21}$ is conducted by treating $\underline{20}$ with an aromatic base such as pyridine, aqueous dimethylsulfoxide, s-collidine or lutidine, in the presence of a displacing agent such as lithium iodide, sodium chloride, sodium bromide, or the like at a temperature of from about 80°-150° C. for from 15 minutes to 2 hours. An aqueous work up of the resulting reaction mixture provides $\underline{21}$. Isomerization of the double bond $\underline{21} \rightarrow \underline{22}$ is accomplished by treating $\underline{21}$ in a solvent such as DMF, DMSO, ethyl ether, THF, glyme, methylene chloride with a strong base such as diisopropylamine, DBU, DBN, or the like at a temperature of from 0° to about 25° C. for from a few minutes to 2 hours or until equilibium has been established as determined by examination of sample aliquots by ultraviolet absorption or by thin layer chromatography.

The final deblocking $\underline{22} \rightarrow I$, may be conducted selectively to preserve the carboxylic ester radical R$^5$ or both R$^9$ and R$^5$ may be removed simultaneously by hydrogenolysis. Typically, $\underline{22} \rightarrow I$, is conducted in a solvent such as dioxane/ethanol/water, or the like in the presence of a platinum metal catalyst such as Pd/C under a hydrogen pressure of from 1 to 5 atmospheres for from 0.25 to 2 hours at a temperature of from 0° to 25° C. Preferred acyl groups, R$^1$, are given below.

The above-described total synthesis may also advantageously start with 4-vinyl azetidinone [(23, below; E. J. Moriconi, W. D. Meyer, *J. Org. Chem.*, 26, 2841 (1971)] rather than the enol acylate azetidinone ($\underline{4}$, above). The following scheme illustrates this 4-vinyl azetidinone embodiment of the present invention; notice that it ties into the above scheme at species $\underline{14}$.

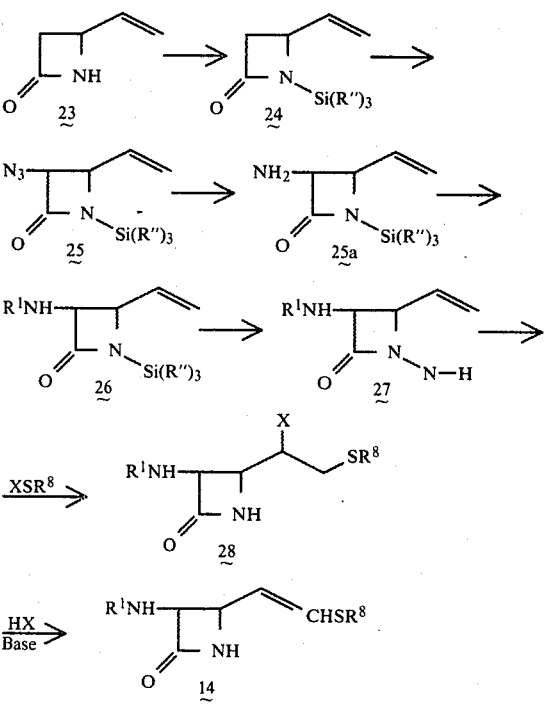

In words relative to the above reaction diagram, 4-vinylazetidinone 23 is silyated to provide the N-silyl species 24. The groups R" on the silyl radical are loweralkyl having from 1-6 carbon atoms especially preferred triorganosilyl groups are trimethyl silyl and t-butyl-dimethylsilyl. Typically, the silylation (23→24) is achieved by treating 23 in a solvent such as DMF, DMSO, HMPA or the like with the silylating agent of choice, dimethyl t-butylsilyl chloride, and a base such as Et₃N, pyridine, N,N-dimethylaniline and the like at a temperature of from −10° to 30° C. for from 1 to 8 hours. Species 24 is converted to 25 by treating with base followed by tosylazide. This reaction 24→25 is conducted exactly as described above for the reaction 7→8. The reduction of 25→25a is accomplished by treating 25 in a solvent such as acetone, THF, dioxane, dimethoxyethane or the like with an excess of triphenylphosphine at 0°-35° C. for a period of 0.5 to 5 hours followed by addition of water and normal work-up. N-acylation of 25a provides 26. The reaction 25a→26 may be accomplished by any of a variety of well-known procedures such as treating 25a in a solvent such as methylene chloride, chloroform or the like with the acid chloride calculated to provide the acyl radical R¹ in the presence of from 1-5 equivalents of pyridine or the like at a temperature of from 0° to 25° C. for from 5-60 minutes. The removal of the N-triorganosilyl group is accomplished in reaction 26→27 by mild acid catalyzed solvolysis. The halo sulfide species 28 is obtained from 27 by treating 27 in a solvent such as methylene chloride, THF, glyme, or the like with the reagent XSR⁸ wherein R⁸ has previously been defined and X is halogen such as chloro or bromo at a temperature of from −50° C. to 50° C. for from 1 to 16 hours. The vinyl sulfide intermediate 14, which is common to the above illustrated scheme of total synthesis is obtained from 28 by elimination of HX on treatment of 28 with a base such as 1,5-diazabicyclo[5.4.0]undec-5-ene(DBU), 1,5-diazabicyclo[4.3.0]non-4-ene, (DBN), 1,4-diazabicyclo [2.2.2]octane, (DABCO), or silver fluoride in a solvent such as DMSO, pyridine DMF, HMPA or the like at a temperature of from −20° C. to 50° C. for from ¼ to 16 hours. Alternatively, in either of the two previous schemes the reduction of the azide and subsequent acylation may be delayed until later in the synthesis. Some alternate points for reduction and acylation are 12, 14, 17, 20, 21 and 22 where R¹NH is still N₃ until the reduction and acylation is accomplished. It should be noted that this N-acyl substituent, R¹, can either be a protecting group or an acyl radical known to be effective in the related penicillin and cephalosporin antibiotic art. When R¹ is a blocking group it is cleaved by well-known procedures at a convenient point in the synthesis, prior to establishment of the preferred R¹ by acylation procedures well-known in the bicyclic β-lactam antibiotic art. The definition of R¹ is more fully given below.

Identification of the Radical —COX'R⁵

In the generic representation of the compounds of the present invention (I, above), the radical represented by —COX'R⁵ is, inter alia, —COOH (X' is oxygen and R⁵ is hydrogen) and all radicals known to be effective as pharmaceutically acceptable ester, anhydride (X' is oxygen and R⁵ is acyl) and amide radicals in the bicyclic β-lactam antibiotic art, such as the cephalosporins and penicillins and the nuclear analogues thereof.

Suitable radicals (R⁵) include conventional protecting or carboxyl blocking groups. The term "blocking group" as utilized herein is employed in the same manner and in accordance with the teaching of U.S. Pat. No. 3,697,515 which is incorporated herein by reference. Pharmaceutically acceptable derivatives of the present invention falling in this class are given below. Suitable blocking esters thus include those selected from the following list which is representative and not intended to be an exhaustive list of possible ester groups, wherein X'=O and R⁵ is given:

(i) R⁵=CRᵃRᵇRᶜ wherein at least one of Rᵃ, Rᵇ and Rᶜ is an electron-donor, e.g., p-methoxyphenyl. The remaining Rᵃ, Rᵇ and Rᶜ groups may be hydrogen or organic substituting groups. Suitable ester groups of this type include p-methoxybenzyloxycarbonyl.

(ii) R⁵=CRᵃRᵇRᶜ wherein at least one of Rᵃ, Rᵇ and Rᶜ is an electron-attracting group, e.g., p-nitrophenyl, trichloromethyl, and o-nitrophenyl. Suitable esters of this type include p-nitrobenzyloxycarbonyl, and 2,2,2-trichloroethoxycarbonyl.

(iii) R⁵=CRᵃRᵇRᶜ wherein at least two of Rᵃ, Rᵇ and Rᶜ are hydrocarbon such as alkyl, e.g., methyl or ethyl, or aryl, e.g., phenyl and the remaining Rᵃ, Rᵇ and Rᶜ group, if there is one, is hydrogen. Suitable esters of this type include t-butyloxycarbonyl, diphenylmethoxycarbonyl and triphenylmethoxycarbonyl.

Silyl esters, under this category of blocking groups, may conveniently be prepared from a halosilane of the formula: R⁴₃SiX' wherein X' is a halogen such as chloro or bromo and R⁴ is alkyl, e.g., methyl, ethyl, t-butyl.

More generally stated, pharmaceutically acceptable carboxyl derivatives of the present invention are those derived by reacting I with alcohols, acylating reagents and the like. For example, esters and amides of interest are the above-listed starting materials and final products having the —COX'R⁵ group at the 2-position; wherein X' is oxygen, sulfur or NR' (R' is H or R⁵), and R⁵ is alkyl having 1-6 carbon atoms, straight or branched, such as methyl, ethyl, t-butyl, and the like; carbonylmethyl, including phenacyl; aminoalkyl including 2-methylaminoethyl, 2-diethylaminoethyl; alkanoyloxyalkyl wherein the alkanoyloxy portion is straight or branched and has 1-6 carbon atoms and the alkyl portion has 1-6 carbon atoms, such as pivaloyloxymethyl; haloalkyl wherein halo is chloro, and the alkyl portion is straight or branched having 1-6 carbon atoms, e.g., 2,2,2-trichloroethyl; alkenyl having 1-4 carbon atoms such as 2-propenyl, 3-butenyl, and 4-butenyl; aralkyl and lower alkoxyl- and nitro- substituted aralkyl such as benzyl, benzhydryl, o-nitrobenzyl, p-methoxybenzyl, and p-nitrobenzyl; phthalidyl; benzyloxyalkyl having 8-10 carbon atoms such as benzyloxymethyl, and (4-nitro) benzyloxymethyl.

In addition to the esters (and thio esters) listed above, amides are also embraced by the present invention, i.e., wherein X' is the

group. Representative of such amides are those wherein R' is selected from the group consisting of hydrogen and lower alkyl such as methyl and ethyl.

The most preferred —COX'R⁵ radicals of the present invention are those wherein (relative to Structure I above), X is oxygen and R⁵ is hydrogen; loweralkyl having 1–4 carbon atoms; lower alkenyl such as 3-methylbutenyl, 4-butenyl and the like; benzyl and substituted benzyl such as p-nitrobenzyl; pivaloyloxymethyl, 3-phthalidyl; and phenacyl.

Identification of the Acyl Radical R¹ of Structure I

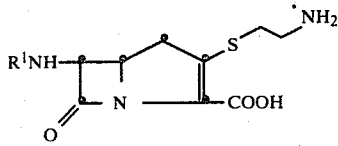

In the generic representation of the compounds of the present invention (I, above), the acyl radical represented by $R^1$ can, inter alia, be substituted or unsubstituted aliphatic, aromatic or heterocyclic, araliphatic or heterocyclylaliphatic carboxylic acid radical, s substituted or unsubstituted carbamyl radical or a carbothioic acid radical. One group of acyl radicals can be represented by the general formula:

wherein X is O or S and R″ represents hydrogen; amino; substituted amino such as alkyl- and dialkyl-amino wherein the alkyl radical comprises 1 to about 6 carbon atoms; substituted or unsubstituted: straight or branched chain alkyl wherein the alkyl radical comprises 1 to about 6 carbon atoms; mercapto such as alkylthio, typically comprising 1 to 6 carbon atoms; arylthio, typically comprising 6 to 10 carbon atoms; hydroxy such as alkoxy, typically comprising 1 to 6 carbn atom; aryloxy, typically comprising 6 to 10 carbon atom; alkenyl, or alkynyl groups typically comprising 2 to 6 carbon atoms; aryl such as phenyl; aralkyl such as benzyl; cycloalkyl, typically comprising 3 to 6 carbon atoms; or a heteroaryl or heteroaralkyl group (mono- and bicyclic) wherein the alkyl moiety typically comprises 1 to 3 carbon atoms and the heterocyclic ring comprises typically 4–10 atoms and the hetero atom or atoms are selected from O,N and S; such above-listed groups can be unsubstituted or can be substituted by radicals such as OH, SH, SR (R is loweralkyl or aryl such as phenyl), alkyl or alkoxy groups having 1 to about 6 carbon atoms, halo, such as Cl, Br, F and I, cyano, carboxy, sulfamino, carbamoyl, sulfonyl, azido, amino, substituted amino such as alkylamino including quaternary ammonium wherein the alkyl group comprises 1 to 6 carbon atoms, haloalkyl such as trifluoromethyl, carboxyalkyl, carbamoylalkyl, N-substituted carbamoylalkyl, wherein the alkyl moiety of the foregoing four radicals comprises 1 to about 6 carbon atoms, amidino, quanidino, N-substituted guanidino, guanidino lower alkyl and the like. Reprsentative examples of such acyl groups that might be mentioned are those wherein R″ is benzyl, p-hydroxybenzyl, 4-amino-4-carboxybutyl, methyl, cyanomethyl, 2-pentenyl, n-amyl, n-heptyl, ethyl, 3- or 4-nitrobenzyl, phenethyl, β,β-diphenylethyl, methyldiphenylmethyl, triphenylmethyl, 2-methoxyphenyl, 2,6-dimethoxyphenyl, 2,4,6-trimethoxyphenyl, 3,5-dimethyl-4-isoxazolyl, 3-butyl-5-methyl-4-isoxazolyl, 5-methyl-3-phenyl-4-isoxazolyl, 3-(2-chlorophenyl)-5-methyl-4-isoxazolyl, 3-(2,6-dichlorophenyl)5-methyl-4-isoxazolyl, D-4-amino-4-carboxybutyl, D-4-N-benzoylamino-4-carboxy-n-butyl, p-aminobenzyl, 0-aminobenzyl, m-aminobenzyl, p-dimethylaminobenzyl, (3-pyridyl)methyl, 2-ethoxy-1-naphthyl, 3-carboxy-2-quinoxalinyl, 3-(2,6-dichlorophenyl)-5-(2-furyl)-4-isoxazolyl, 3-phenyl-4-isoxazolyl, 5-methyl-3-(4-quanidinophenyl)-4-isoxazolyl, 4-guanidinomethylphenyl, 4-guanidinomethyl-benzyl, 4-guanidinobenzyl, 4-guanidinophenyl, 2,6-dimethoxy-4-guanidino, o-sulobenzyl, p-carboxymethylbenzyl, p-carbamoylmethylbenzyl, m-fluorobenzyl, m-bromobenzyl, p-chlorobenzyl, p-methoxybenzyl, 1-naphthyl-methyl, 3-isothiazolylmethyl, 4-isothiazolylmethyl, 5-isothiazolylmethyl, guanylthiomethyl, 4-pyridylmethyl, 5-isoxazolylmethyl, 4-methoxy-5-isoxazolylmethyl, 4-methyl-5-isoxazolylmethyl, 1-imidazolylmethyl, 2-benzofuranylmethyl, 2-indolylmethyl, 21-phenylvinyl, 2-phenylethynyl, 1-aminocyclohexyl, 2- and 3-thienylaminomethyl, 2-(5-nitrofuranyl)vinyl, phenyl, o-methoxyphenyl, o-chlorophenyl, o-phenylphenyl, p-aminomethylbenzyl, 1-(5-cyanotriazolyl)methyl, difluoromethyl, dichloromethyl, dibromomethyl, 1-(3-methylimidazolyl)methyl, 2- or 3-(5-carboxymethyl-thienyl)methyl, 2- or 3-(4-carbamoylthienyl)methyl, 2- or 3-(5-methylthienyl)methyl, 2- or 3-(methoxythienyl)-methyl, 2- or 3-(4-chlorothienyl)-methyl,2- or 3-(5-sulfothienyl)methyl, 2- or 3-(5-carboxythienyl)methyl, 3-(1,2,5-thiadiazolyl)methyl, 3-(4-methoxy-1,2,5-thiadiazolyl)methyl, 2-furylmethyl, 2-(5-nitrofuryl)-methyl, 3-furylmethyl, 2-theinylmethyl, 3-thienyl-methyl, tetrazolylmethyl benzamidinomethyl and cyclohexylamindinomethyl.

The acyl group can also be a radical of the formula:

wherein X is O or S and n is 0–4, Z represents oxygen, sulfur, carbonyl or nitrogen and R″ is defined as above. Representativve member of the substituent

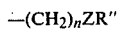

that might be mentioned are allylthiomethyl, phenylthiomethyl, butylmercaptomethyl, α-chlorocrotylmercaptomethyl, phenoxymethyl, phenoxyethyl, phenoxybutyl, phenoxybenzyl, diphenoxymethyl, dimethylmethoxymethyl, dimethylbutoxymethyl, dimethylphenoxymethyl, 4-guanidinophenoxymethyl, 4-pyridylthiomethyl, p-(carboxymethyl)phenoxymethyl, p-(carboxymethyl)phenylthiomethyl, 2-thiazolylthiomethyl, p-(sulfo)phenoxymethyl, p-(carboxymethyl)phenylthiomethyl, 2-pyrimidinylthiomethyl, phenethylthiomethyl, 1-(5,6,7,8-tetrahydronaphthyl)oxomethyl, N-methyl-4-pyridylthio, benzyloxy, methoxy, ethoxy, phenoxy, phenylthio, amino, methylamino, dimethylamino, pyridinium methyl, trimethylammoniummethyl, cyanomethylthiomethyl, trifluoromethylthiomethyl, 4-pyridylethyl, 4-pyridylpropyl, 4-pyridylbutyl, 3-imidazolylethyl, 3-imidazolylpropyl, 3-imidazolylbutyl, 1-pyrroloethyl, 1-pyrrolopropyl and 1-pyrrolobutyl.

Alterntively, the acyl group can be a radical of the formula:

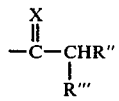

wherein R" is defined as above and R''' is a radical such as amino, hydroxy, azido, carbamoyl, guanidino, amidino, acyloxy, halo, such as Cl, F, Br, I, sulfamino, tetrazolyl, sulfo, carboxy, carbalkoxy, phosphono and the like. Representative members of the substituent

that might be mentioned are α-aminobenzyl, α-amino-(2-thienyl)methyl, α-(methylamino)benzyl, α-aminomethylmercaptopropyl, α-amino-3- or 4-chlorobenzyl, α-amino-3- or 4-hydroxyenzyl, α-amino-2,4-dichlorobenzyl, α-amino-3,4-dichlorobenzyl, D(—)-α-hydroxybenzyl, α-carboxybenzyl, α-amino-(3-thienyl)methyl D-(—)-α-amino-3-chloro-4-hydroxybenzyl, α-amino(cyclohexyl)methyl, α-(5-tetrazolyl)-benzyl, 2-thienylcarboxymethyl, 3-thienyl-carboxymethyl, 2-furylcarboxymethyl, 3-furyl-carboymethyl, α-sulfaminobenzyl, 3-thienyl-sulfaminomethyl, α-(N-methylsulfamino)-benzyl, D(—)-2-thienyl-guanidinomethyl, D(—)-α-guanidinobenzyl, α-guanylureidobenzyl, α-hydroxybenzyl, α-azidobenzyl, α-fluorobenzyl, 4-(5-methoxy-1,3-oxadiazolyl)-aminomethyl, 4-(5-methoxy-1,3-oxadiazolyl)-hydroxymethyl, 4-(5-methoxy-1,3-sulfadiazolyl)-hydroxymethyl, 4-(5-chlorothienyl)aminomethyl, 2-(5-chlorothienyl)-hydroxymethyl, 2-(5-chlorothienyl)-carboxy-methyl, 3-(1,2-thiazolyl)-aminomethyl 3-(1,2-thiazolyl)-hydroxymethyl, 3-(1,2-thiazolyl)-carboxymethyl, 2-(1,4-thiazolyl)-aminomethyl, 2-(1,4-thiazolyl)-hydroxymethyl, 2-(1,4-thiazolyl)-carboxymethyl, 2-benzothienylaminomethyl, 2-benzothienylhydroxymethyl, 2-benzothienylcarboxymethyl, α-sulfobenzyl, α-phosphonobenzyl, α-diethylphosphono and α-monoethylphosphono. Further acyl radicals of interest in this class when X=oxygen are:

wherein $R^3$ and $R^4$ are as defined below. $R^3$ represents hydrogen, halo, such as chloro, fluoro, bromo, iodo, amino, guanidino, phosphono, hydroxy, tetrazolyl, carboxy, sulfo, or sulfamino and $R^4$ represents pheyl, substituted phenyl, a mono- or bicyclic heterocyclyl containing one or more oxygen, sulfur or nitrogen atoms in the ring, such as furyl, quinoxalyl, thienyl, quinolyl, quinazolyl, thiazolyl, isothiazolyl, tetrazolyl, oxadiazolyl, thiadiazolyl and the like substituted heterocycles, phenylthio, phenyloxy, lower alkyl or 1–6 carbon atoms, heterocyclic or substituted heterocyclic thio groups; or cyano. The substituents on the moieties, $R^3$ and $R^4$, can be halo, carboxymethyl, guanidino, guanidinomethyl, carboxamidomethyl, aminoethyl, nitro, methoxy or methyl. When $R^3$ is selected from the group consisting of hydrogen, hydroxy, amino or carboxy and $R^4$ is selected from the group consisting of phenyl, or a 5- or 6-membered heterocyclic ring having one or two sulfur, oxygen or nitrogen hetero atom such as tetrazolyl, thienyl, furyl and phenyl, the following acyl radicals are representative: phenylacetyl, 3-bromophenylacetyl, p-aminomethylphenylacetyl, 4-carboxymethylphenylacetyl, 4-carboxyamidomethylphenylacetyl, 2-furylacetyl, 5-nitro-2-furylacetyl, 3-furylacetyl, 2-thienylacetyl, 5-chloro-2-thienylacetyl, 5-methoxy-2-thienylacetyl, α-guanidino-2-thienylacetyl, 3-thienylacetyl, 2-(4-methylthienyl)acetyl, 3-isothiazolylacetyl, 4-methoxy-3-isothiazolylacetyl, 4-isothiazolylacetyl, 3-methyl-4-isothiazolylacetyl, 5-isothiazolylacetyl, 3chloro-5-isothiazolylacetyl, 3-methyl-1,2,5-oxadiazolylacetyl, 1,2,5-thiadiazolyl-4-acetyl, 3-methyl-1,2,5-thiadiazolylacetyl, 3-chloro-1,2,5-thiadiazolylacetyl, 3-methoxy-1,2,5-thiadiazolylacetyl, phenylthioacetyl, 4-pyridylthioacetyl, cyanoacetyl, 1-tetrazolylacetyl, α-fluorophenylacetyl, D-phenylglycyl, 4-hydroxy-D-phenylglycyl, 2-thienylglycyl, 3-thienylglycyl, phenylmalonyl, 3-chlorophenylmalonyl, 2-thienylmalonyl, 3-thienylmalonyl, α-phosphonophenylacetyl, α-amino cyclohexadienylacetyl, α-sulfaminophenylacetyl, α-hydroxyphenylacetyl, α-tetrazolylphenylacetyl and α-sulfophenylacetyl.

$R^1$ of Structure I may also be a readily removable protecting group; a particularly preferred acyl for this purpose is o or p-nitrobenzyloxycarbonyl.

Relative to the generic expression of the compounds of the present invention (I):

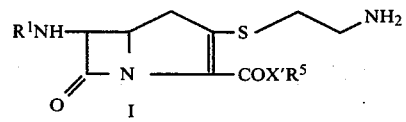

The radicals $R^1$ and/or —$COX'R^5$ may be established after synthesis, rather than being established during the course of synthesis, by operating upon the 6-amino group and/or the carboxyl group. Ester embodiments involving the carboxyl group are conveniently prepared by conventional procedures known in the art. Such procedures include:

1. Reaction of I with a diazoalkane such as diazomethane, phenyldiazomethane, diphenyldiazomethane and the like in an inert solvent such as dioxane, THF, halohydrocarbons, acetonitrile, ethylacetate, and the like at a temperature of from −78° C. to 25° C. for from a few minutes to 2 hours.

2. Reaction of the metallic salts (e.g., Na, Li) of the acid I with an activated alkyl halide such as methyliodide, benzylbromide, or m-phenoxybenzylbromide, p-t-butylbenzylbromide, m-phenoxybenzylbromide, and the like. Suitable reaction conditions include inert, anhydrous polar non-protic solvents such as hexamethylphosphoramide, DMF, THF, dioxane, and the like at a temperature of from −78° C. to 25° C. for from a few minutes to 4 hours.

The above-recited schemes of esterification are well known in the related bicyclic β-lactam antibiotic art and indeed in all of general organic synthesis is and it is to be noted that there is no undue criticality of reaction parameters in the preparation of the compounds of the present invention.

Establishment of the radical $R^1$ may alternatively be established prior to deblocking the amino group of the N-protected 3-(2-aminoethylthio) group by selectively deblocking to obtain a free amine at position 6 of I and acylating to establish the desired, pharmacologically effective acyl radical $R^1$ by conventional procedures.

The products of this invention (I) form a wide variety of pharmacologically acceptable salts with inorganic and organic bases; these include, for example, metal salts derived from alkali or alkaline earth metal hydroxides, carbonates or bicarbonates and salts derived from primary, secondary or tertiary amines such as monoalkylamines, dialkylamines, trialkylamines, lower alkanolamines, di-lower-alkanolamines, lower alkylenediamines, N,N-diaralkyl lower alkylenediamines, aralkylamines, amino substituted lower akanols, N,N-di-lower alkylamino substituted lower alkanols, amino-, polyamino- and guanidino-substituted lower akanoic acids and nitrogen-containing heterocyclic amines. Representative examples include salts derived from sodium hydroxide, sodium carbonate, sodium bicarbonate, potassium carbonate, potassium hydroxide, calcium carbonate, trimethylamine, triethylamine, piperidine, morpholine, quinine, lysine, protamine, arginine, procaine, ethanolamine, morphine, benzylamine, ethylenediamine, N,N'-dibenzylethylenediamine, diethanolamine, piperazine, dimethylaminoethanol, 2-amino-2-methyl-1-propanol, theophylline, N-methylglucamine and the like. Acid addition salts, e.g., with hydrochloric, tartaric, hydrobromic, sulfuric, nitric, toluene-p-sulphonic and methane sulphonic acids may also be employed.

The salts can be mono-salts such as the monosodium salt obtained by treating one equivalent of sodium hydroxide with one equivalent of the product (I), also mixed di-salts. Such salts may be obtained by treating one equivalent of a base having a divalent cation, such as calcium hydroxide, with one equivalent of the product (I). The salts of this invention are pharmacologically acceptable nontoxic derivatives which can be used as the active ingredient in suitable unit-dosage pharmaceutical forms. Also, they may be combined with other drugs to provide compositions having a broad spectrum of activity.

The compounds of the present invention are valuable antimicrobial substances which are active against various gram-positive and gram-negative pathogens. Thus the free acid, free base, and especially the salts thereof such as amine and metal salts, particularly the alkali metal and alkaline earth metal salts, are useful bactericides and can be used for removing susceptible pathogens from dental and medical equipment, for separating microorganisms, and for therapeutic use in humans and animals. For this latter purpose pharmacologically acceptable salts with inorganic and organic base such as those known in the art and used for the administration of penicillins and cephalosporins can be utlized. For example, salts such as alkali metal and alkaline earth metal salts and primary, secondary and tertiary amine salts can be used for this purpose. These salts can be combined with pharmaceutically acceptable liquid and solid vehicles to form suitable dosage unit forms such as pills, tablets, capsules suppositories, syrups, elixirs and the like which can be prepared in accordance with procedures well known in this art.

The novel compounds are valuable antibiotics active against various gram-positive and gram-negative bacteria, and accordingly, find utility in human and veterinary medicine. The compounds of this invention can therefore be used as antibacterial drugs for treating infections caused by gram-positive or gram-negative bacteria, for example against *Staphylococcus aureus, Escherichia coli, Klebsiella pneumoniae, Bacillus substilis, Salmonella typhosa, Pseudomonas* and *Bacterium proteus.* The antibacterials of the invention may further be utilized as additives to animal feedingstuffs, for preserving foodstuffs and disinfectants. For examle, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example in waterbased paints and in the white water of paper mills to inhibit the growth of harmful bacteria.

The products of this invention may be used alone or in combination as an active ingredient in any one of a variety of pharmaceutical preparations. These antibiotics and their corresponding salts may be employed in capsule form or as tablets, powders or liquid solutions or as suspensions or elixirs. They may be administered orally, intravenously or intramuscularly.

The compositions are preferably presented in a form suitable for absorption by the gastro-intestinal tract. Tablets and capsules for oral administration may be in unit dose presentation form, and may contain conventional excipients such as binding agents, for example, syrup, acacia, gelatin, sorbitol, tragacanth, or polyvinylpyrrolidone; fillers for example, lactose, sugar, maize-starch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solutions, emulsions, syrups, elixiers, etc. or may be presented as a dry product, for reconstitution with water or other suitable vehicles before use. Such liquid preparations may contain conventional additives such as suspending agents, for example sorbitol syrup, methyl cellulose, glucose/sugar syrup, gelatin, hydroxyethylcellulose, carboxymethyl cellulose, aluminum stearate gel or hydrogenated edible oils, for example almond oil, fractionated coconut oil, oily esters, propylene glycol, or ethyl alcohol; preservatives, for example methyl or propyl p-hydroxybenzoates or sorbic acid. Suppositories will contain conventional suppository bases, e.g. cocoa butter or other glyceride.

Compositions for injection may be presented in unit dose form in ampules, or in multidose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form for reconstitution with a suitable vehicle, e.g. sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops etc. Topical applications may be formulated in hydrophobic or hydrophilic bases as ointments, creams, lotions, paints, powders, etc.

Also, in addition to a carrier, the instant compositions may include other ingredients such as stabilizers, binders, antioxidants, preservatives, lubricators, suspending agents, viscosity agents or flavoring agents and the like. In addition, there may also be included in the composition other active ingredients to provide a broader spectrum of antibiotic activity.

For veterinary medicine the composition may, for example, be formulated as an intramammary preparation in either long acting or quick-release bases.

The dosage to be administered depends to a large extent upon the condition of the subject being treated and the weight of the host, the route and frequency of administration, the parenteral route being preferred for generalized infections and the oral route for intestinal infections. In general, a daily oral dosage consists of from about 5 to about 600 mg. of active ingredient per kg. of body weight of the subject in one or more applications per day. A preferred daily dosage for adult humans lies in the range of from about 15 to 240 mg. of active ingredient per kg. of body weight.

The instant compositions may be administered in several unit dosage forms as, for example, in solid or liquid orally ingestible dosage form. The compositions per unit dosage, whether liquid or solid may contain from 0.1% to 99% of active material, the preferred range being from about 10–60%. The composition will generally contain from about 15 mg. to about 1500 mg. of the active ingredient; however, in general, it is preferable to employ a dosage amount in the range of from about 250 mg. to 1000 mg. In parenteral administration the unit dosage is usually the pure compound in a slightly acidified sterile water solution or in the form of a soluble powder intended for solution.

The following examples, illustrate but do not limit the product, process, compositional or method of treatment aspects of the present invention.

EXAMPLE 1

Preparation of 4-(2-acetoxyvinyl)azetidinone-2-one

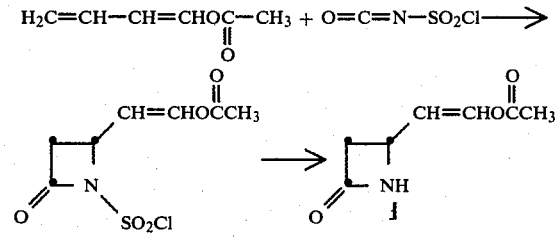

A solution of 1.0 ml distilled chlorosulfonylisocyanate (1.65 g; 11.7 mmoles) in 2.5 ml anhydrous diethyl ether is cooled under $N_2$ in a $-20°$ C. bath.

A solution of 2.5 g 1-acetoxybutadiene (22 mmoles) in 2.5 ml anhydrous ether is similarly cooled under $N_2$ in a $-20°$ C. bath.

The chlorosulfonylisocyanate solution is added dropwise to the acetoxybutadiene solution by means of a Teflon tube immersed in the CSI solution and pressurized with $N_2$. The addition takes 10 minutes. Little or no color is seen and the reaction is stirred at $-20°$ C. for 0.5 hour. The solution is clear and has a light yellow color.

A solution of 2 g sodium sulfite and 5 g $K_2HPO_4$ in 20 ml $H_2O$ is prepared during the above 0.5 hour reaction time and is cooled in an ice bath; 20 ml of ether is added and the mixture is vigorously stirred in an ice bath. At the end of the 30 minute reaction time, the reaction mixture is transferred, again using $N_2$ pressure and the Teflon tube, from the reaction flask which is maintained in the $-20°$ C. bath, to the vigorously stirred hydrolysis mixture. Rapid dropwise addition is completed in 5 minutes. The hydrolysis is allowed to continue for 5 additional minutes. The hydrolysis mix has a pH of 6–8, preferably pH 8.

The phases are separated, leaving a yellowish-orange gum with the aqueous phase. The ether phase is dried directly with $MgSO_4$. The aqueous/gum phase is extracted three more times with 50 ml portions of ether, each being added to the initial ether/$MgSO_4$.

The dried extracts are filtered and concentrated under a $N_2$ stream to 5 ml; a portion of the product is crystalline at this stage.

A column of 10 g Baker silica gel, packed in ether is prepared, and the ether concentrate is applied to the top and run in. The flask/solids are rinsed three times with 2 ml ether, each being pipetted off and run into the column. Elution is then begun with ether. The first 25 ml is primarily void volume. The next five 10 ml fractions are collected followed by three 50 ml fractions, and all are reduced in volume under a $N_2$ stream. The product crystallizes from fractions 4–6, with traces in 3 and 7. Fractions 1–3 contain a yellowish sharp-smelling material which resinifies on standing. Yield: 100 mg as a mixture of the cis and trans isomers.

EXAMPLE 2

Preparation of 4-(2-Acetoxyethyl)-2-Azetidinone

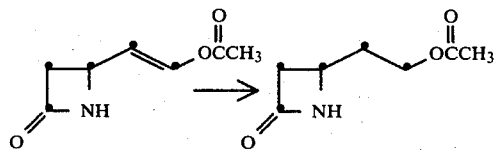

A solution of 4-(2-acetoxyvinyl)-2-azetidinone (10.0 g, 0.065 mole) in 200 ml ethyl acetate containing 100 mg of 10% Pd/C is hydrogenated on a Parr shaker at 25° C. under 40 psi hydrogen for 15 minutes. The mixture is filtered through a bed of Supercel and washed with additional ethyl acetate. The combined filtrate is evaporated in vacuo to give 4-(2-acetoxyethyl)-2-azetidinone (10.0 g) as a crystalline solid. Recrystallization from ether affords white crystals: M.P. 44°–7°; ir $(CHCl_3)_\mu$ 5.66, 5.74; nmr $(CDCl_3)$ $\tau$ 3.44 (broad s, 1, NH), 5.82 (m, 2, $CH_2OCOCH_3$), 6.29 (m, 1, C-4H), 6.87 ($\frac{1}{2}$ AB pattern further split in four by C-4H and NH, 1, $J_{gem}=12.8$ Hz, J=4.5 H $J_{NH}=1.9$ Hz, 7.38 ($\frac{1}{2}$ AB pattern further split in four by C-4H and NH, 1, $J_{gem}=12.8$ Hz, J=2.3 Hz, $J_{NH}=1.0$ Hz), 7.93 and 8.02 (s on m, total 5, $OCOCH_3$ and $CH_2CH_2OCOCH_3$, respectively).

EXAMPLE 3

Preparation of 4-(2-Hydroxyethyl)-2-Azetidinone

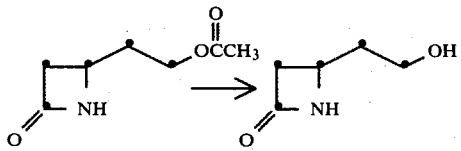

Under nitrogen at 0°, a solution of 4-(2-acetoxyethyl)-2-azetidinone (2.24 g, 0.014 mole) in 25 ml anhydrous methanol is treated with a solution of sodium methoxide (77 mg, 1.4 mmoles) in 5 ml anhydrous methanol. After stirring for 1 hour, the solution is neutralized with glacial acetic acid. Removal of the methanol in vacuo gives crude 4-(2-hydroxyethyl)-2-azetidinone as an oil. The product is purified by chromatography on silica gel eluting with 10% MeOH/CHCl₃ to give 1.55 g of the alcohol: m.p. 50°; ir (CHCl₃) μ 5.67; nmr (CDCl₃) τ 3.20 (broad s, 1, NH), 6.24 and 6.28 (m on t, total 3, C-4H and CH₂OH respectively), 6.90 (broad s on ½ AB pattern further split in four by C-4H and NH, total 2, OH and C-3H respectively, $J_{gem}$=13.0 Hz, $J_{vic}$=4.2 Hz, $J_{NH}$=1.6 Hz), 7.42 (½ AB pattern further split in four by C-4H and NH, 1, C-3H, $J_{gem}$=13.0 Hz, $J_{vic}$=2.2 Hz, $J_{NH}$=1.1 Hz), 8.16 (m, 2, CH₂CH₂OH).

EXAMPLE 4

Preparation of 8-Oxo-2,2-dimethyl-3-oxa-1-azabicyclo[4.2.0]octane

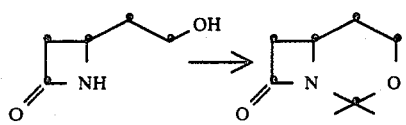

A solution of 4-(2-hydroxyethyl)-2-azetidinone (1.87 g, 0.016 mole) and 2,2-dimethoxypropane (1.69 g, 0.016 mole) in 25 ml anhydrous methylene chloride is treated with boron trifluoride etherate (0.201 ml, 0.002 mole) at 25° C. The resulting solution is stirred for ten minutes. Removal of the solvent under reduced pressure gives an oil (2.5 g). Chromatography of the crude product on silica gel using 2:1 ethyl acetate/benzene as eluting solvent gives 8-oxo-2,2-dimethyl-3-oxa-1-azabicyclo[4.2.0]octane (1.59 g) as a crystalline solid. Recrystallization from ether/hexane gives product of m.p. 60°-1°. ir (CHCl₃)μ:5.73 (β-lactam)

| nmr (CDCl₃)τ: | 6.02-6.28, m, 2H, C-4 methylene |
|---|---|
| | 6.22-6.62, m, 1H, C-6 methine |
| | 6.90, dd, 1H, $J_{7,7}$ = 14Hz, $J_{6,7}$ = 4.5Hz C-7 proton cis to C-6H |
| | 7.47, dd, 1H, $J_{7,7}$ = 14Hz, $J_{6,7}$ = 2Hz C-7 proton trans to C-6H |
| | 7.82-8.68, m, 2H, C-5 methylene |
| | 8.23, s, 3H ⎫ C-2 methyls |
| | 8.57, s, 3H ⎭ |

EXAMPLE 5

Preparation of 7-amido-8-oxo-2,2-dimethyl-3-oxa-1-azabicyclo[4.2.0]octane

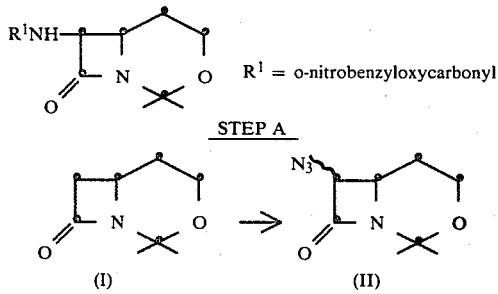

A solution of 1.54 ml (11 mmoles) of diisopropylamine in 30 ml of dry THF is cooled to −78° C. in dry-ice/acetone bath; 6.11 ml (11 mmoles) of 1.8 M methyllithium is added dropwise under nitrogen. The resulting solution is stirred at the same temperature for 1 hour; 1.55 g (10 mmol) of the bicyclic azetidinone I in 10 ml of dry THF is added dropwise. The mixture is stirred for 1 hr at −78° C. Then, 2.17 g (11 mmoles) of tosyazide in 5 ml of dry THF is added dropwise. The resulting mixture is warmed to −50° C. and kept for 1.5 hrs at that temperature; 2.54 ml (20 mmol) of trimethylchlorosilane is added and the mixture is heated at reflux for 6 hrs. The reaction mixture is cooled and the solid is filtered off and washed with 2×25 ml of ether. The filtrate is concentrated. The residue is taken up in 100 ml of water and extracted with 3×25 ml of methylene chloride. The combined extracts are dried over anhydrous MgSO₄ and concentrated to give a glue which is chromatographed on silica gel (eluant 50:50 ethylacetate:cyclohexane) to give the desired 7-azido-8-oxo-2,2-dimethyl-3-oxa-1-azabicyclo[4.2.0]octane, II, as a solid (45% yield).

STEP B

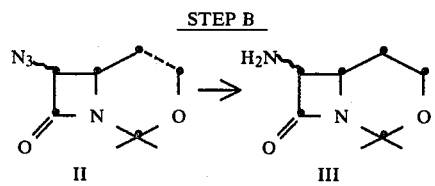

The azetidinone II (1.96 g) is dissolved in 50 ml of ethylacetate and 100 mg of 10% Pd on carbon is suspended. The azide is then shaken in a Parr shaker in an atmosphere of hydrogen at 4.5 psi at 25° C. After 24 hr, the catalyst is filtered off on 'supercel' and the filtrate is concentrated to give the amine III.

STEP C

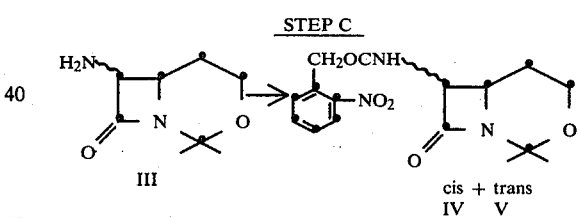

The amine resulting from Step B is dissolved in 50 ml of CH₂Cl₂ and cooled to 0° C. in an ice bath, 800 μl of pyridine is then added. After 5 minutes, 2.155 g of o-nitrobenzyloxycarbonyl chloride is added dropwise. The reaction mixture is warmed to 25° C. over a period of 1 hr. and washed with 2×25 ml of water. The organic phase is dried over MgSO₄, and concentrated to give a gum, which is chromatographed on silica gel eluting with ethylacetate in cyclohexane to separate the cis and trans- carbamate IV & V.

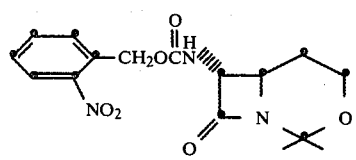

nmr: (CDCl₃/C₆-DMSO); δ; 7.47 - 8.4 (aromatic); 5.43 s(benzyl CH₂); 4.33 dd(J=2; J=8) (C7-H, trans); 1.39 & 1.61 (s(CH₃).

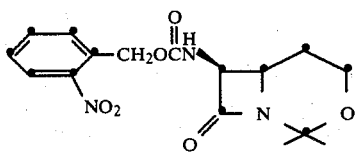

nmr: (CDCl₃/D₆-DMSO); δ; 7.4 - 8.3 (aromatic); 5.43 s(benzyl CH₂); 4.9 dd(J=4.5; J=8); C7-H; cis); 1.4 & 1.65 s(CH₃).

EXAMPLE 6

Preparation of 7-phenylacetamido-8-oxo-2,2-dimethyl-3-oxa-1-azabicyclo[4.2.0]octane

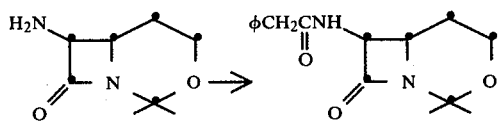

The amine resulting from Example 5, Step B is dissolved in 50 ml of CH₂Cl₂ and cooled to 0° C. in an ice bath; 800 μl of pyridine is then added. After 5 minutes, 1.54 g of phenylacetyl chloride is added dropwise. The reaction mixture is warmed to 25° C. over a period of 1 hour and washed with 2×25 ml of water. The organic phase is dried over MgSO₄, and concentrated. The residue is chromatographed on silica gel to give 7-phenylacetamido-8-oxo-2,2-dimethyl-3-oxa-1-azabicyclo[4.2.0]octane.

EXAMPLE 7

Preparation of 3-phenylacetamido-4-(2-hydroxyethyl)-2-azetidinone

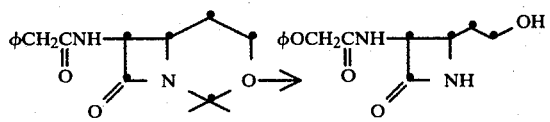

8-Oxo-3-oxa-2,2-dimethyl-7-phenylacetamido-1-azabicyclo[4.2.0]octane (0.76 g) is dissolved in 8 ml acetic acid and 2 ml water and heated at 65° C. for 1.25 hours. The acetic acid and water are removed under reduced pressure and the residue is taken up in benzene and evaporated to give 3-phenylacetamido-4-(2-hydroxyethyl)-2-azetidinone.

EXAMPLES 8–11

Examples 8, 9, 10 and 11 as alternative to Examples 4, 5, 6 and 7 for the preparation of 3-phenylacetamido-4-(2-hydroxyethyl)-azetidinone

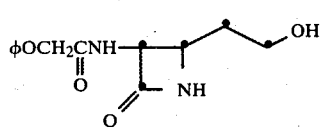

EXAMPLE 8

Preparation of 1-(2-Tetrahydropyranyl)-4-[2-(2-tetrahydropyranyl)oxyethyl]-2-azetidinone

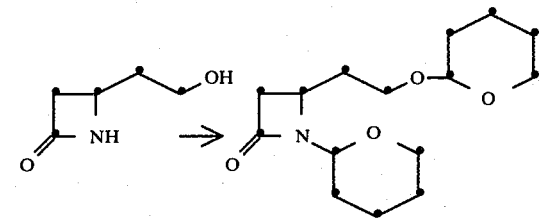

Under nitrogen and at 25° C., a solution of 4-(2-hydroxyethyl)-2-azetidinone (62 mg, 0.539 mmole) in 0.5 ml of anhydrous p-dioxane is treated with 2,3-dihydropyran (0.98 ml, 1.08 mmoles) and p-toluenesulfonic acid monohydrate (19 mg, 0.10 mmole). The resulting solution is stirred for a period of 60 minutes and then partitioned between 10 ml of 0.5 M pH7 phosphate buffer and 0.10 ml of ethyl acetate. The aqueous phase is extracted a second time with ethyl acetate. The combined ethyl acetate solutions are washed with brine, dried over magnesium sulfate and filtered. The filtrate is evaporated under reduced pressure to give 216 mg of crude product. Purification by preparative thick-layer chromatography developing with ethyl acetate gives 80 mg of 1-(2-tetrahydropyranyl)-4-[2-(2-tetrahydropyranyl)oxyethyl]-2-azetidinone as an oil.

nmr (CDCl₃)τ:  5.13–5.60, m, OC<u>H</u>
5.83–6.85, m, C—4H + OC<u>H</u>₂

6.95, dd, J = 5Hz and 15 Hz  }  C—3 methylene
7.35, dd, J = 3Hz and 15 Hz 7.62–8.95, m, CHC<u>H</u>₂C<u>H</u>₂C<u>H</u>₂CH₂ + CHC<u>H</u>₂CH₂O

EXAMPLE 9

Preparation of 1-(2-tetrahydropyranyl)-3-azido-4-[2-(2-tetrahydropyranyl)oxyethyl]-2-azetidinone

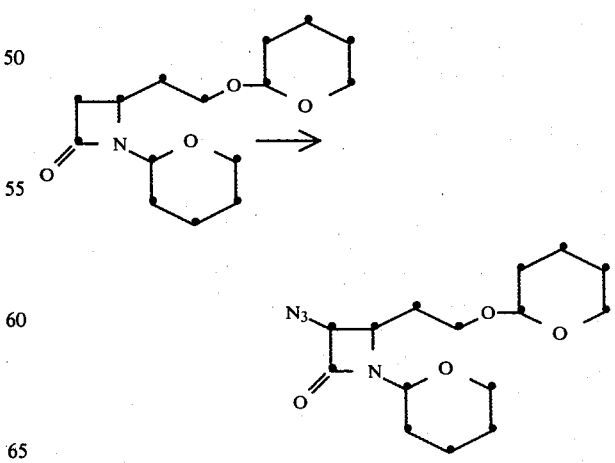

Following the procedure described for the preparation of 7-azido-8-oxo-2,2-dimethyl-3-oxo-1-azabicyclo[4.2.-

0]octane from 8-oxo-2,2-dimethyl-3-oxa-1-azabicyclo[4.2.0]octane (Example 5, Step A) and using 1-(2-tetrahydropyranyl)-4-[2-(2-tetrahydropyranyl)oxyethyl]-2-azetidinone one obtains 1-(2-tetrahydropyranyl)-3-azido-4-[2-(2-tetrahydropyranyl)-oxyethyl]-2-azetidinone.

EXAMPLE 10

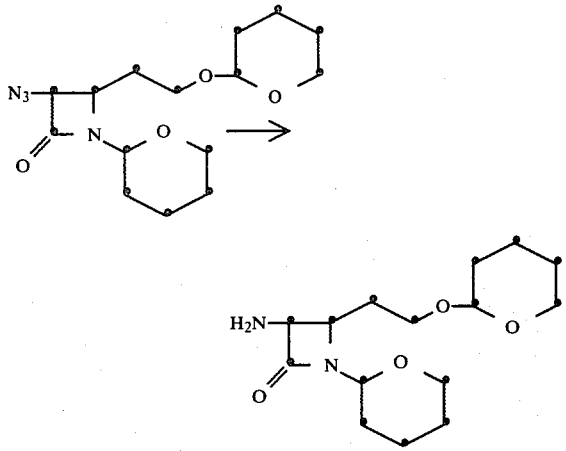

Following the procedure described for the preparation of 7-amino-8-oxo-2,2-dimethyl-3-oxa-1-azabicyclo[4.2.0]octane from 7-azido-8-oxo-2,2-dimethyl-3-oxa-1-azabicyclo[4.2.0]octane (Example 5, Step B) and using 1-(2-tetrahydropyranyl)-3-azido-4-[2-(2-tetrahydropyranyl)oxyethyl]-2-azetidinone there is obtained 1-(2-tetrahydropyranyl)-3-amino-4-[2-(2-tetrahydropyranyloxyethyl]-2-azetidinone.

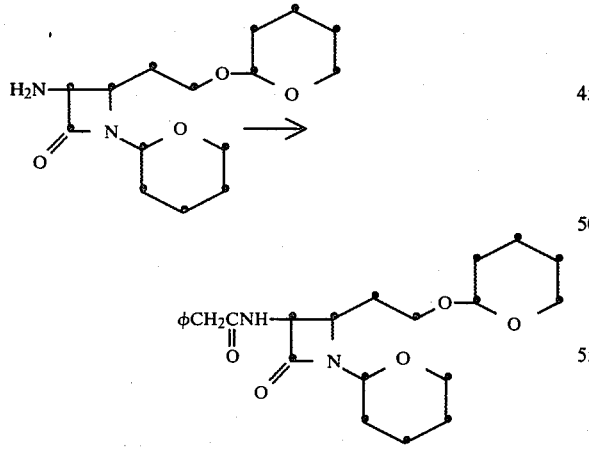

Following the procedure described for the preparation of 7-phenylacetamido-8-oxo-2,2-dimethyl-3-oxa-1-azabicyclo[4.2.0]octane from 7-amino-8-oxo-2,2-dimethyl-3-oxa-1-azabicyclo[4.2.0]octane (Example 6) and using 1-(2-tetrahydropyranyl)-3-amino-4-[2-(2-tetrahydropyranyl)oxyethyl]-2-azetidinone there is obtained 1-(2-tetrahydropyranyl)-3-phenylacetamido-4-[2-(2-tetrahydropyranyl)oxyethyl]-2-azetidinone.

EXAMPLE 11

Preparation of 3-Phenylacetamido-4-(2-hydroxyethyl)-2-azetidinone

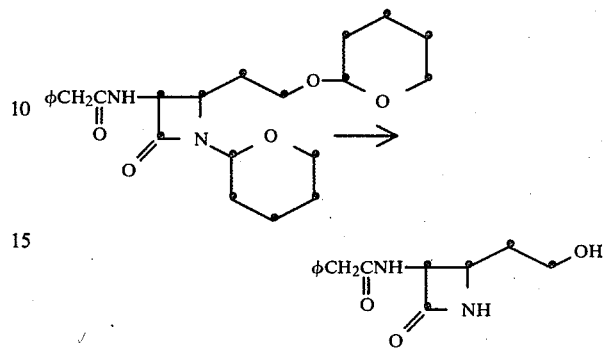

A solution of 1-(2-tetrahydropyranyl)-3-phenylacetamido-4-[2-(2-tetrahydropyranyl)oxyethyl]-2-azetidinone in methanol at 25° C. is treated with 0.1 molar equivalent of p-toluenesulfonic acid monohydrate. The solution is stirred for a period of 2 hours and then neutralized with 1 M pH 7 phosphate buffer. The product is extracted into ethyl acetate. The ethyl acetate solution is washed with brine, dried over magnesium sulfate and filtered. The filtrate is evaporated under reduced pressure to give 3-phenylacetamido-4-(2-hydroxyethyl)-2-azetidinone.

EXAMPLE 12

Preparation of 3-(2-aminoethylthio)-6phenylacetamido-7-oxo-1-azabicyclo-[3.2.0]hept-2-ene-2-carboxylic acid

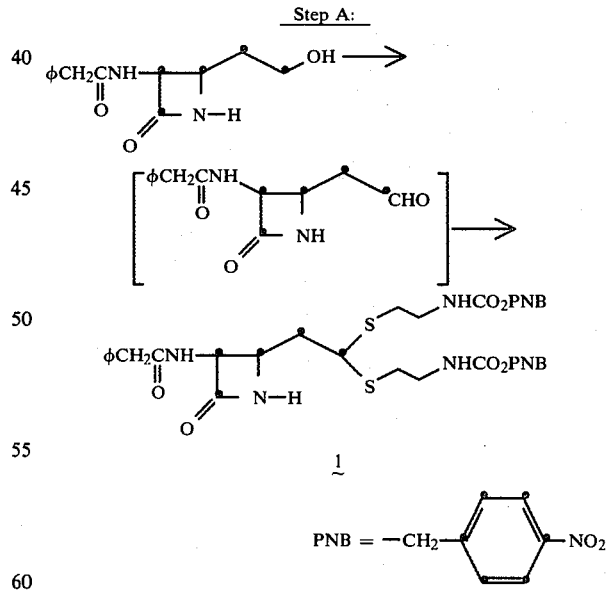

To 6.75 ml anhydrous pyridine (mw=79; ρ-0.982; 83.9 mmole) in 350 ml anhydrous acetonitrile is added 4.05 g anhydrous powdered chromium trioxide (mw=100; 40.5 mmole). After stirring at room temperature (25° C.) for 30 minutes, 9.6 g dried Supercell is added and stirring is continued for 5 additional minutes. A solution of 2.36 g 3-phenylacetamido-4-(2-hydroxyethyl)-2-azetidinone (mw=248; 9.5 mmole) in 30 ml anhydrous acetonitrile is added all at once. The reaction mixture is stirred under anhydrous conditions at room temperature (25° C. for one hour. Addition of 9.6 g NaHSO$_3$ is followed by 5 minutes of stirring after which the reaction mixture is filtered through a mixed packed bed of 40 g silica gel and 40 g anhydrous magnesium sulfate. The bed is washed repeatedly with acetonitrile (total volume of filtrate ~600 ml). The filtrate is concentrated under a N$_2$ stream to 130 ml total volume. To this solution containing crude aldehyde at 0° C. under N$_2$ is added 9.64 g p-nitrobenzyloxycarbonylaminoethanethiol (mw=256; 37.7 mmole) as prepared below, (Example 12, Step B). To the stirred reaction mixture is added 8.0 ml boron trifluoride etherate (mw=142; $\rho$=1.125; 63.4 mmole). After 1.5 hours at 0° C., the reaction mixture is poured into a stirred ice-cold mixture of 69 g K$_2$HPO$_4$-500 ml H$_2$O and 700 ml ethyl acetate (EA). The layers are separated, and the aqueous one is saturated with NaCL and re-extracted with additional EA. The combined organic layers are washed twice with brine, dried over anhydrous MgSO$_4$ and filtered. The filtrate is concentrated under a N$_2$ stream and then pumped on high vacuum to give crude $\underline{1}$.

The material is chromatographed on 450 g silica gel. (Column height=48 cm; diameter=5.5 cm) packed and applied in CHCl$_3$ and eluted with increasing percentages of MeOH in CHCl$_3$. Those fractions containing the desired product are combined, concentrated under a N$_2$ stream; and pumped on high vacuum to give $\underline{1}$.

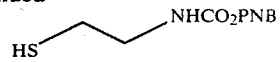

To 600 ml diethyl ether(Et$_2$O) - 75 ml H$_2$O in an ice bath with stirring is added 3.2 g cysteamine hydrochloride (mw=114; 28.1 mmole). A solution of 7.14 g NaHCO$_3$ (mw=84; 85 mmole) in 75 ml H$_2$O is added. The ice bath is removed, and at room temperature a solution of 6.75 g p-nitrobenzylchloroformate (mw=216; 31.3 mmole) in 270 ml Et$_2$O is added dropwise over a period of one hour. After 10 additional minutes, the layers are separated. The ether layer is extracted with 150 ml 0.25 N HCl, and then with 200 ml brine. Each aqueous layer is then backwashed successively with 100 ml Et$_2$O. The combined Et$_2$O layers are dried over anhydrous MgSO$_4$, filtered, and concentrated under a N$_2$ stream. The crystalline residue is slurried in a small amunt of ether, filtered, and the pale yellow crystals are dried under high vacuum to give 4.7 g p-nitrobenzyloxycarbonylaminoethanethiol (65% yield).

NMR (CDCl$_3$): 8.18 (d, J=8 Hz, aromatic protons ortho to nitro), 7.47 (d, J=8 Hz, aromatic protons meta to nitro), 5.27 (—NH—), 5.20 (s, —C$\underline{H}_2$-$\phi$-pN0$_2$), 3.40 (m, —C$\underline{H}_2$—NH—), 2.67 (m, —C$\underline{H}_2$—SH), 1.35 (t, J=8.5 Hz, —S$\underline{H}$) in ppm downfield from TMS.

IR (CHCl$_3$ solution) carbonyl-~1725 cm$^{-1}$.

M.S. - molecular ion-256, (m-47) at 209, (M-136) at 120, +CH$_2$$\phi$pNO$_2$ at 136.

STEP C

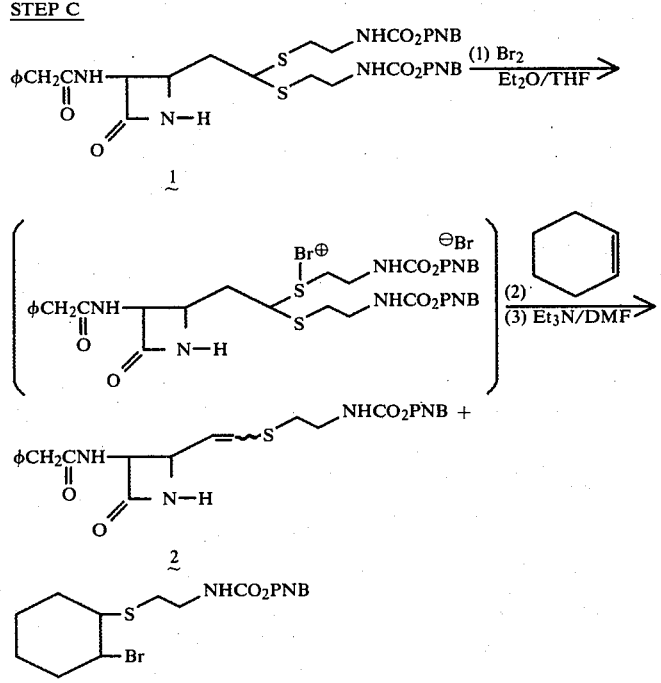

Step B
Preparation of p-Nitrobenzyloxycarbonylaminoethanethiol

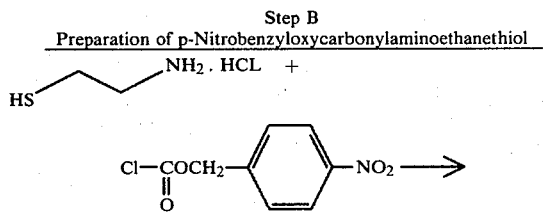

To 14.2 ml pentane (dried over 4A Linde molecular sieves) is added 0.5 ml Br$_2$ (mw=160; 9.75 mmole). To 4.45 g of $\underline{1}$ (mw=740; 6.02 mmole) in 58 ml tetrahydrofuran (THF) (freshly distilled from lithium aluminum hydride) (LAH) and 65 ml Et$_2$O (dried over 3A 1/16" Linde molecular sieves) at 0° C. under N$_2$ with stirring is added dropwise 10 ml of the above 0.66 M Br$_2$ solution (6.6 mmole). After 10 minutes at 0° C., 0.67 ml cyclohexene (mw=82; $\rho$=0.81; 6.6 mmole) is added. After 5 minutes at 0° C., 1.7 ml triethylamine (mw=101; ρ=0.729; 12.3 mmole) is added immediately followed by 40 ml ice-cold dimethylformamide (DMF) (distilled from anhydrous CaSO₄ at 40 mm and stored over 4A Linde molecular sieves). The ice bath is removed, and stirring is continued for 2¼ hours at room temperature. The reaction mixture is poured into a stirred ice-cold mixture of 12.6 ml 1 MKH₂PO₄ 160 ml H₂O-500 ml (EA). After separation of the layers, the aqueous one is saturated with sodium chloride and re-extracted with EA. The combind organic layers are extracted once with brine, dried over anhydrous MgSO₄, filtered and concentrated under a N₂ stream followed by pumping under high vacuum to provide crude 2̰.

The material is chromatographed on 250 g silica gel height=45 cm; diameter=4.5 cm) packed and applied in CHCl₃ and eluted with increasing percentages of MeOH in CHCl₃. Those fractions containing clean product are combined, concentrated under a N₂ stream, and pumped on high vacuum to give 2̰.

STEP D:

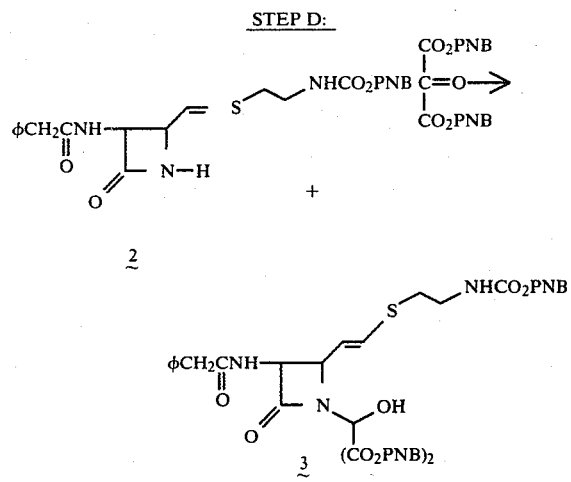

To a stirred solution of 2.48 g di(p-nitrobenzyl) ketomalonate (from Example 12, Step E) (mw=388; 6.39 mmole) in 400 ml hot anhydrous toluene is added a solution of 2.12 g of 2̰ (mw=484; 4.39 mmole) in 20 ml THF (distilled from LAH) and 40 ml anhydrous toluene. After some of the solvent is boiled off, additional anhydrous toluene is added, and the azeodrying process is repeated three times. The solution is then refluxed under N₂ for 30 minutes. Additional toluene is then allowed to boil off yet the volume is not allowed to diminish so much that precipitation occurs. Total heating time is approximately 2½ hours. The reaction is removed from the oil bath and placed under a stream of N₂. After concentration, the residue is dissolved in CH₂Cl₂, dried over anhydrous MgSO₄, filtered, and concentrated under a N₂ stream to give crude 3̰.

The material is chromatographed on 250 g silica gel packed and applied in CHCl₃ (height=43 cm; diameter=4.5 cm, eluting with MeOH/CHCl₃. Those fractions containing pure 3̰ are combined, concentrated under a N₂ stream and then on high vacuum to give 3̰.

Later fractions containing 3̰ and the corresponding cis thioenol ether are re-chromatographed on silica gel to give additional 3̰.

STEP E
Preparation of di-p-Nitrobenzyl Ketomalonate

-continued

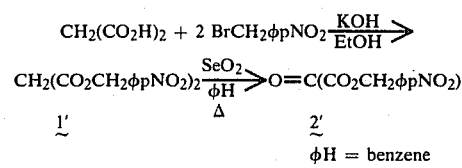

φH = benzene

A mixture of 100 g p-nitrobenzyl bromide (0.46 mole), 28.6 g malonic acid (0.275 mole) and 750 ml ethanol (EtOH) is stirred and warmed on the steam bath until solution is achieved. A solution of 33 g KOH (>85% purity; ~0.6 mole) in 200 ml of water is added carefully with swirling. An additional 200 ml of water is added, and the tow-phase system is refluxed for 1.8 hours. The lighter color homogeneous solution is cooled in ice for 1 hour and the crude product isolated by filtration, washed twice with a minimum of cold EtOH, and dried by pulling dry N₂ through the cake; 33.7 g of solid is obtained. If, during the refluxing stage the reaction mixture is slowly concentrated to ca. half volume by allowing refluxing solvent to distill off, the crude product yield rises to 77 g. The material is recrystallized from methanol to give pure di-p-nitrobenzyl malonate 1̰'.

A mixture of 23.4 of 1̰', 10 g SeO₂, and 30-40 ml of xylene is stirred in a flask immersed in an oil bath. The bath temperature is raised over 1 hour to 130°-135°. A gradual darkening of the reaction mixture is noted, and after a total of 4 hours at 130°-135°, most of the insoluble residue is black Se°. The mixture is cooled, MgSO₄ is added to remove the water, and Celite is added to aid in filtration. The mixture is filtered through Celite and the cake washed with xylene and a small portion of EtOAc. Final volume: 60 ml. A 100 g column of Baker Silica Gel is prepared in benzene and 10 ml of filtrate applied, then eluted with increasing amounts of EtOAc in benzene, 500 ml fractions being collected. After one 2% ethyl acetate (EtOAc)/φH, and two 10% EtOAc/φH fractions, the third 10% and first 20% EtOAc/φH provide the bulk of the product (~1.6 g from 10 ml filtrate) as judged by tlc (20% EtOAc/CHCl₃; silica gel GF). Recrystallization from benzene, (1 g in ca. 50 ml concentrated to ~⅓ volume and "spiked" with 1 ml of H₂O saturated benzene): provides 0.24 g 2̰'; mp(117) 121°-122°.

STEP F

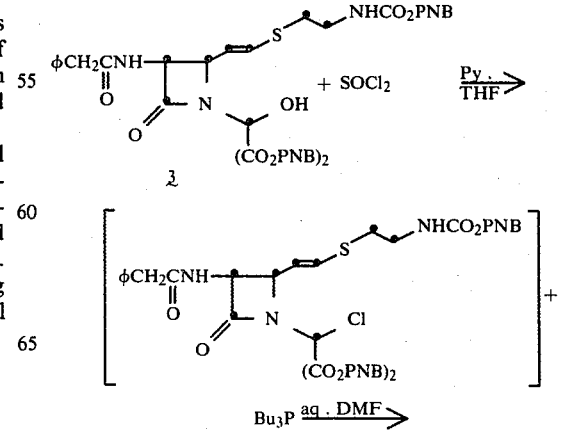

-continued

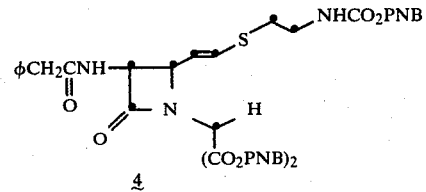

4

-continued

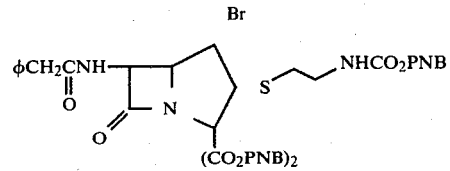

5

A solution of 1.33 g. of 3 (mw=872; 1.53 mmole) in CH$_2$Cl$_2$ is dried over anhydrous MgSO$_4$, filtered, concentrated under a N$_2$ stream, and dried further under high vacuum just prior to the following reaction. To a solution of 3 in 24 ml THF (freshly distilled from LAH) at −20° C. is added 0.206 ml anhydrous pyridine (mw=79; ρ=0.982; 2.56 mmole). With stirring under N$_2$, 294 mg of freshly distilled thionyl chloride (mw=119; 2.47 mmole) in 5 ml THF is added dropwise. The reaction mixture is stirred for 10 minutes at −20° C., then ½ hour at 0° C. and finally 1 hour at 25° C. The pyridine hydrochloride is filtered under N$_2$ and washed with 20 ml THF. The filtrate is concentrated under N$_2$ stream followed by pumping on high vacuum. The residue is swirled in 25 ml anhydrous THF, and any insoluble material is filtered off under N$_2$. The filtrate is re-concentrated as above to a foam.

To this freshly prepared chloro compound is added with stirring a freshly shaken suspension of 678 mg tributylphosphine (mw=202; 3.36 mmole) in 36.5 ml 9:1 DMF - H$_2$O followed by 294 mg K$_2$HPO$_4$ (mw=174; 1.69 mmole). The reaction mixture is stirred at 25° C., for 35 minutes. After dilution with 120 ml EA and 60 ml brine, the layers are separated, and the aqueous one is extracted two times with EA. The combined organic layers are washed one time with brine, dried over anhydrous MgSO$_4$, filtered and concentrated under a N$_2$ stream followed by pumping on high vacuum to give crude 4.

The material is chromatographed on 100 g silica gel (height=28.5 cm; d=4 cm) packed and applied in CHCl$_3$ and eluted with MeOH in CHCl$_3$. Those fractions containing clean product are combined, concentrated under a N$_2$ stream and then on high vacuum to give 4.

STEP G

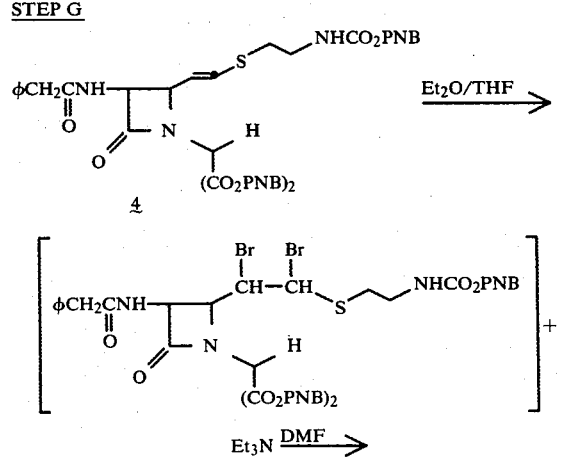

To 8.5 ml pentane (dried over 4A Linde molecular sieves) is added 0.2 ml Br$_2$ (mw=160; 3.9 mmole). To 0.639 g of 4 (mw=856; 0.746 mmole) in 18 ml THF (freshly distilled from LAH) and 5.7 ml Et$_2$O (dried over 3A 1/16" Linde molecular sieves) at 0° C. under N$_2$ with stirring is added dropwise 1.8 ml of the above 0.45 M Br$_2$ solution (0.81 mmole). After 15 minutes at 0° C., 0.42 ml triethyl amine (mw=101; ρ=0.729; 3.03 mmole) is added immediately followed by 10.5 ml ice-cold DMF (distilled from CaSO$_4$ at 40 mm and stored over 4A Linde molecular sieves). The ice-bath is removed, and stirring at room temperature is continued for 2 hous. The reaction mixture is poured into a stirred ice-cold mixture of 3.1 ml 1 M KH$_2$PO$_4$—70 ml H$_2$O—100 ml Ea. The layers are separated, and the aqueous one is saturated with NaCl and re-extracted with EA. The combined organic layers are washed once with brine, dried over anhydrous MgSO$_4$, and filtered. The filtrate is concentrated under a N$_2$ stream and then pumped on high vacuum to give crude 5.

The material is chromatographed on 60 g silica gel (diameter=2.8 cm) packed and applied in CHCl$_3$ and is eluted with EA/CHCl$_3$. The fractions containing 5 are combined, concentrated under a N$_2$ stream, and pumped on high vacuum to give 5.

STEP H

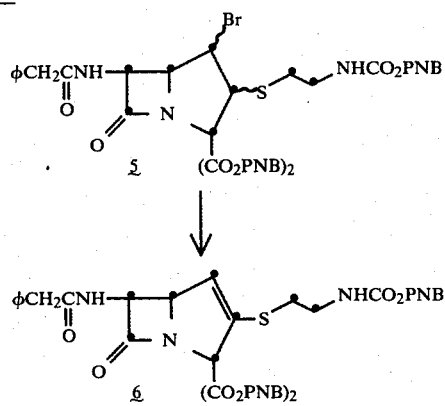

To 29 mg anhydrous silver fluoride (mw=127; 0.23 mmole) is added a solution of 131 mg of 5 (mw=984; 0.14 mmole) in 3.5 ml anhydrous pyridine. The stoppered reaction mixture is stirred at room temperature in the dark for one hour and then poured into 20 ml cold water—30 ml EA. After separation of the layers, the aqueous one is extracted two times with EA and one time CHCl$_3$. Each organic layer is extracted one time with H$_2$O and one time with brine. The combined organic layers are dried over anhydrous MgSO$_4$, filtered, and concentrated under a N$_2$ stream followed by pumping on high vacuum to give crude 6.

Preparative thin layer chromatography yields 6.

STEP I

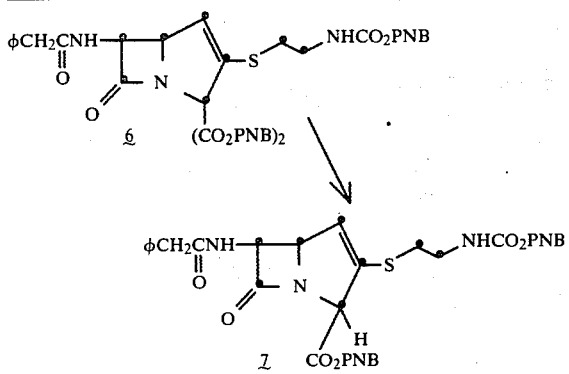

A solution of 70 mg of 6 (mw=854; 0.082 mmole) in 0.9 ml S-collidine (distilled from powdered KOH~30 mm pressure) is added to 13.4 mg anhydrous LiI (dried for few hours at 100° C. over $P_2O_5$ under vacuum) (mw=134; 0.1 mmole). With stirring under $N_2$, the reaction mixture is heated in an oil bath at 120° C. After a total of 30 minutes, the reaction mixture is cooled to 25° C., diluted with $CH_2Cl_2$, and transferred to a round bottom flask for concentration under a $N_2$ stream and then on high vacuum. Partitioning the residue between EA-$H_2O$ and 1 ml 1 M $KH_2PO_4$ is followed by extraction of the aqueous layer two additional times with EA and one time with $CHCl_3$. Each organic layer is then backwashed with brine. The combined organic layers are dried over anhydrous $MgSO_4$, filtered, concentrated under a $N_2$ stream and then on high vacuum to give crude 7.

Preparative thin layer chromatography on silica gel yields 7.

STEP J

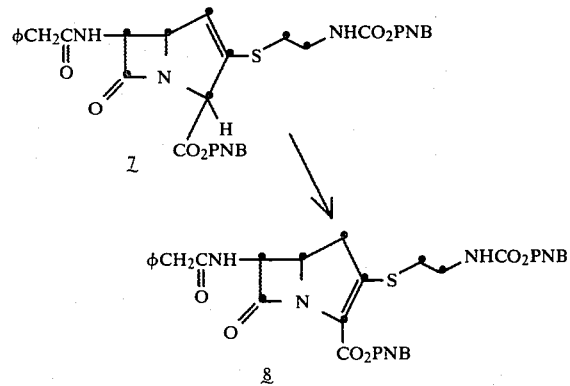

To 43 mg of 7 (m=675; 0.064 mmole) in 0.7 ml DMSO (distilled from $CaH_2$ at 8 mm and stored over 4A Linde molecular sieves) is added 100 μdiisopropylamine (distilled from NaH under $N_2$ and stored over 4A Linde molecular sieves) (Mw=101; ρ=0.722; 0.71 mmole). The stoppered reaction mixture is stirred for a few minutes and then allowed to stand for 2 hours. The amine and most of the DMSO are then concentrated off under high vacuum with no external heating. The residue is passed quickly through a a column of silica gel (packed, applied, and eluted with EA) to remove residual DMSO. After concentration under a $N_2$ stream of all fractions having u.v. absorbance, the material is chromatographed on a thin layer silica gel plate. The product band yields 8. Starting material is re-submitted to the reaction conditions and isolation procedure two more times to yield additonal 8.

STEP K

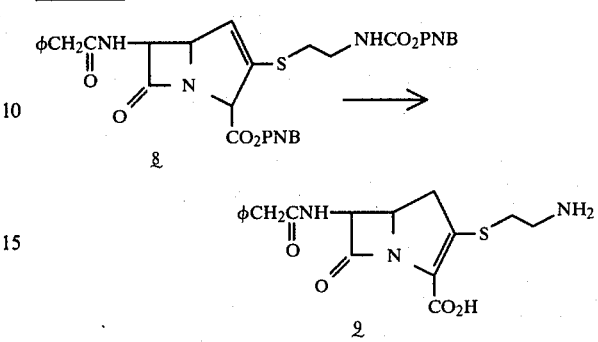

To 4.6 mg 8 is added 0.60 ml dioxane, 0.05 ml ethanol, 0.35 ml deionized water and 0.01 ml of 1.0 M $K_2HPO_4$. To the resultant clear solution is added 5 mg of 10% Pd/c. The suspension if flushed with $N_2$, then 5-6 times alternately with 50 psi $H_2$ and vacuum. Finally it is shaken under a 50 psi $H_2$ atmosphere for 30-40 min. After centrifugation, the Pd/C is washed and centrifuged 2-3× with 0.5 ml portions of deionized water. The combined centrifugates are extracted 5×1-2 ml ether. Residual either is removed under vacuum and the aqueous solution applied to an XAD-2 column (20×140 mm). Fractions of 100 drops (6-7 ml) are collected, with continuous UV monitoring, by elution with deionized water. Emergence of strongly UV absorbing material begins around fractions 3-5 and is usually complete by fractions 25-30. Early fractions are examined by UV to exclude those few deemed too strongly absorbing in the 270-280 mμ region. The remaining fractions are combined and lyophilized. The residue is evaluated by dissolving in 10.0 ml of deionized water and measuring the UV absorbtion at 298 mμ indicating the presence of desired product.

EXAMPLE 13

STEP A

Preparation of 24 [1-(t-butyldimethylsilyl)-4-vinyl-2-azetidinone

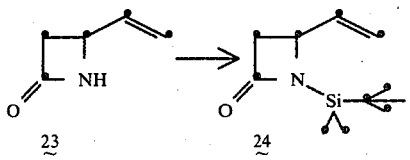

A solution of 23 [4-vinyl-2-azetidinone] (1.153 g, 11.89 mmoles) and triethylamine (1.82 ml, 13.08 mmoles) in anhydrous N,N-dimethylformamide is placed under a nitrogen atmosphere, cooled to 0° C. and treated with t-butyldimethylchlorosilane (1.885 g, 12.48 mmoles) resulting in the immediate appearance of a heavy white precipitate. This mixture is stirred for one hour while gradually warming to room temperature. The mixture is partitioned between 30 ml. methylene chloride and 90 ml cold 1M potassium dihydrogen phosphate. The aqueous phase is extracted with 20 ml methylene chloride. The combined organic phases are washed four times with 30 ml portions of water and finally with 50 ml brine. The methylene chloride solution is dried over anhydrous magnesium sulfate and filtered. The filtrate is evaporated under reduced pressure to give 24 [1-(t-butyldimethylsilyl)-4-vinyl-2-azetidinone].

STEP B
Preparation of 25, 1-(t-butyldimethysilyl)-3-azido-4-vinyl-2-azetidinone

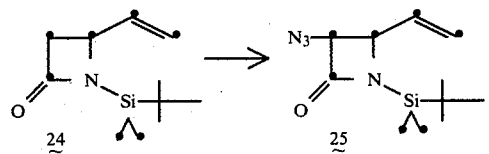

Following the procedure described for the preparation of 7-azido-8-oxo-2,2-dimethyl-3-oxa-1-azabicyclo[4.2.0]-octane from 8-oxo-2,2-dimethyl-3-oxa-1-azabicyclo[4.2.0]-octane (Example 5, Step A) and using 1-(t-butyldimethylsilyl)-4-vinyl-2-azetidinone there is obtained 1-(t-butyldimethylsilyl)-3-azido-4-vinyl-2-azetidinone.

STEP C
Preparation of 26, 1-(t-butyldimethylsilyl)-3-phenyl-acetamido-4-vinyl-2-azetidinone

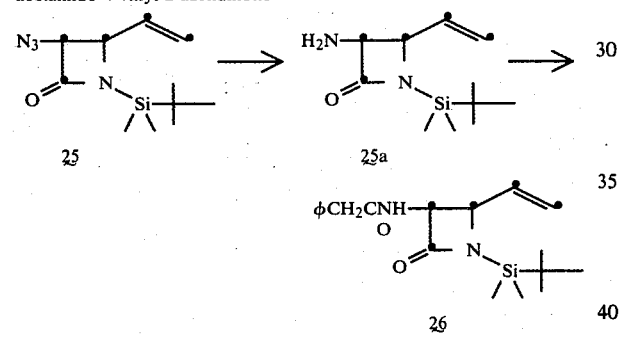

Under anhydrous conditions at room temperature a solution of 38 mg of the azide in 1.0ml of acetone is treated with a 90% excess of triphenyl phosphine (75 mg). After 4 hrs, 100 μl water is added with continued stirring for 90 min. The solution is concentrated in vacuo to dryness. The residue, containing crude amine, 25a, is dissolved in methylene chloride, dried over anhydrous MgSO₄, and filtered. The filtrate is exposed to the procedure for the preparation of 7-phenylacetamido-8-oxo-2,2-dimethyl-3-oxa-1-azabicyclo[4.2.0]octane (Example 6) to give 26.

STEP D
Desilylation of 26 to provide 27 [3-phenylacetamido)-4-vinyl-2-azetidnone]

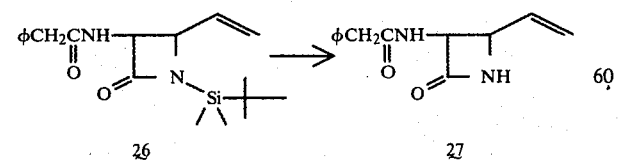

A solution of 26 [1-(t-butyldimethylsilyl)-3-phenylacetamido-4-vinyl-2-azetidinone] (49 mg, 0.141 mmole) in 2 ml of 0.5N HCl/MeOH is stirred at room temperature (25° C.) for a period of 3 hours. The solution is then cooled to 0° C. and neutralized by the addition of 5 ml of 5% aqueous sodium bicarbonate. The product is extracted into ethyl acetate (10 ml, 2×5 ml). The combined ethyl acetate solutions are washed with water (2×5 ml) and 10 ml brine and then dried over anhydrous magnesium sulfate. The drying agent is removed by filtration, and the filtrate is evaporated in vacuo. Preparative thick-layer chromatography of this material on silica gel gives 27, [3-phenylacetamido-4-vinyl-2-azetidinone].

STEP E:
Preparation of 14 via 28 by sulfenyl halide addition and dehydrohalogenation

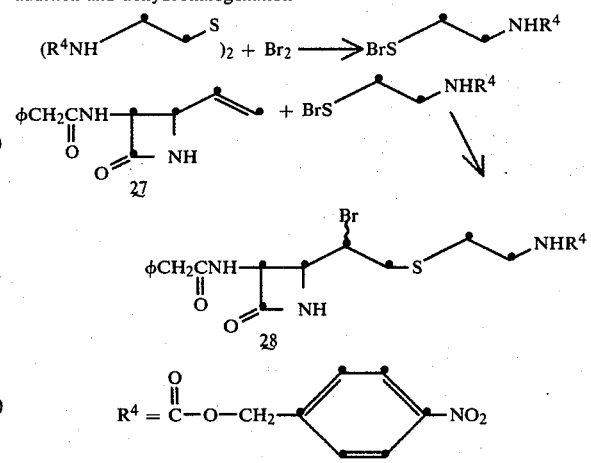

A solution of the N-p-nitroCBz cysteamine disulfide, 96 mg (0.19 mmoles) in 1.5 ml THF (freshly distilled from LiAlH₄) is cooled to −25° C. and treated dropwise with stirring with 0.5 ml of a solution of 135 mg Br₂ in sieve dried CCl₄ (2.2 ml final volume; portion added is equivalent to 0.19 mmoles of Br₂). The resultant orange solution is stirred at −20° C. for 5 min. then treated with 39 mg of the vinyl azetidinone, 27, in 0.5 ml sieve dried CH₂Cl₂. The mixture is allowed to come to 0° C. over 5–10 minutes. The reaction mixture is concentrated to 0.5 ml under N₂ and streaked directly on two 8"×8"1000μ silica GF plate. The product band is extracted with EA to give 28.

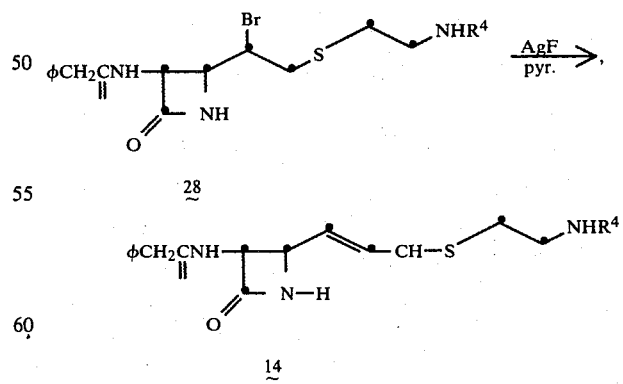

Under nitrogen at room temperature a solution of 35 mg of the bromosulfide, 28 in 0.5 ml pyridine is treated in the dark with 17 mg of silver fluoride. The mixture is stirred for 2 hours and then is partitioned between 2 ml EA & 10 ml H.O. The aqueous phase is extracted two more times with EA and the combined ethyl acetate solutions are filtered through a bed of supercel which is eluted with additional EA. The clear filtrate is washed one time with brine, dried over anhydrous MgSO4, filtered and evaporated in vacuo to give crude 14. Chromatography on silica gel gives purified 14.

EXAMPLE 14

Preparation of Bis (p-Nitrobenzyloxycarbonylaminoethyl)disulfide

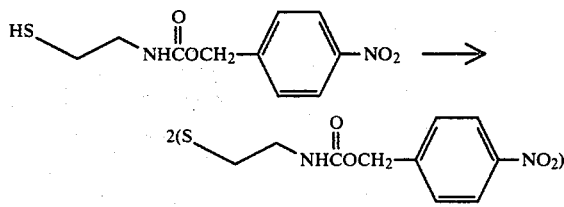

Under nitrogen at −20° C., bromine (1.21 ml, 0.022 mmole) is added to a solution of p-nitrobenzyloxycarbonylaminoethanethiol (11.28g, 0.044 mmole) in 100 ml of anhydrous tetrahydrofuran. The cooling bath is removed, and the cold solution is stirred for 15 minutes. The solution is then diluted with 400 ml ethyl acetate and washed 200 ml 1 M pH 7 phosphate buffer, 200 ml 1 M dibasic potassium phosphate, water (2×200 ml, 100 ml) and 200 ml brine. It is dried over anhydrous magnesium sulfate and filtered. The filtrate is evaporated in vacuo giving a yellow solid residue. This material is chromatographed on silica gel eluting with 5% ethyl acetate/chloroform to give 10.5 g of crystalline bis (p-nitrobenzyloxycarbonylaminoethyl)disulfide:

IR (CH2Cl2)μ:3.04 NH 5.96 carbonyl 6.22, 6.61 nitro.

| NMR (CDCl3)δ: | 8.24 | } d, J = 8.5Hz, ArH |
| --- | --- | --- |
|  | 7.54 |  |
|  | 5.37, | broad s, NH |
|  | 5.26, | s, ArCH2O |
|  | 3.60, | q, J = 6Hz and 6Hz, NHCH2CH2 |
|  | 2.86, | t, J = 6Hz, NHCH2CH2S |

EXAMPLE 15

Step A:

Preparation of 3-azido-4-(2-hydroxyethyl)-2-azetidinone

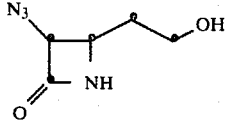

Following the procedure of Example 7 except substituting for the indicated 7-phenylacetamido-8-oxo-2,2-dimethyl-3-oxa-1-azabicyclo[4.2.0]octane the 7-azido-8-oxo-2,2-dimethyl-3-oxa-1-azabicyclo[4.2.0]octane, the title compound is obtained.

Step B:

Preparation of 6-azido-3-(3-p-nitrobenzyloxycarbonylaminoethylthio)-7-oxo-1-azabicyclo[3.2.0]hept-2-ene-2-carboxylic acid, p-nitrobenzylester.

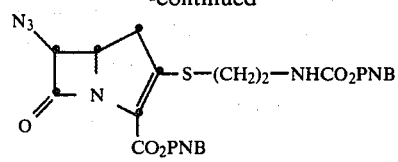

Following the procedures of Example 12, Steps A-J except substituting for the indicated azetidinone the azetidinone of Example 15, Step A, the title compound is obtained.

STEP C

Preparation of 6-phenylacetamido-3-(3-p-nitrobenzyloxycarbonylaminoethylthio)-7-oxo-1-azabicyclo[3.2.0]hept-2-ene-2-carboxylic acid, p-nitrobenzyl ester

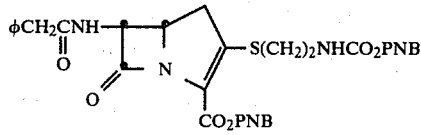

The azide of Example 15, Step B is dissolved in acetone and treated with an excess of triphenyl phosphine under anhydrous conditions with stirring at room temperature for a few hours. Addition of water is followed by further stirring for ½ to a few hours. The reaction mixture is concentrated in vacuo to dryness. The crude amine is dissolved in methylene chloride, dried over anhydrous MgSO4, and filtered. The filtrate is cooled to 20° C., and an equivalent of pyridine is added followed by the dropwise addition of an equivalent of phenylacetylchloride. After stirring for 3 hours, the reaction mixture is shaken twice with water. The resulting organic phase is dried over anhydrous MgSO4. Filtration followed by evaporation in vacuo gives the crude amide. Chromatography on silica gel gives the title compound.

EXAMPLE 16

STEP A

Preparation of 3-azido-4-vinyl-2-azetidinone

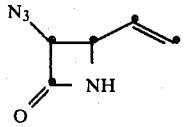

Following the procedure of Example 13, Step D except substituting for the indicated azetidinone the azetidinone prepared in Example 13, Step B, 3-azido-1-(t-butyldimethylsilyl)-4-vinyl-2-azetidinone, the title compound is obtained.

STEP B

Preparation of 6-azido-3-(3-p-nitrobenzyloxycarbonylamino ethylthio)-7-oxo-1-azabicyclo-[3.2.0]hept-2-ene-2-carboxylic acid, p-nitrobenzyl ester

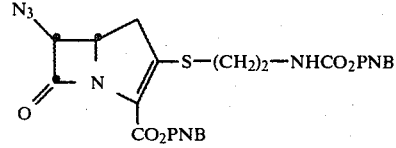

Following the procedures of Example 13, Step E and then Example 12, Steps D–J but substituting for the indicated azetidinone, the azetidinone of Example 16, Step A, the title compound is obtained.

EXAMPLE 17

Preparation of 6-o-Nitrobenzyloxycarbonylamino-3-(p-nitrobenzyloxycarbonylaminoethylthio)-7-oxo-1-azabicyclo[3.2.0-]hept-2-ene-2-carboxylic acid, p-nitrobenzyl ester

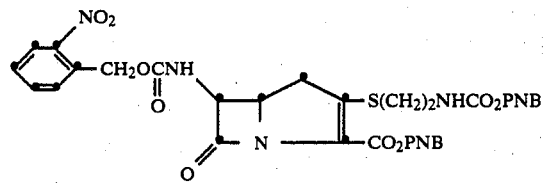

Following the procedures of Example 7 and then Example 12, Steps A–J except substituting for 7-phenylacetamido- 8-oxo-2,2-dimethyl-3-oxa-1-azabicyclo[4.2.0]-octane the 7-o-nitrobenzyloxycarbonylamino-8-oxo-2,2-dimethyl-3-oxa-1-azabicyclo[4.2.0]octane prepared in Example 5 Step C, the title compound is obtained.

EXAMPLE 18

Following the procedure of the foregoing Examples and text, the following species of the invention are obtained by analogy:

| Compound | $R^1$ | $R^4$ |
|---|---|---|
| (1.) | $\phi CH_2 C(=O)-$ | Na |
| (2.) | $\phi CH_2 C(=O)-$ | H |
| (3.) | $\phi CH_2 C(=O)-$ | H |
| (4.) | $\phi CH_2 C(=O)-$ | Na |
| (15.) | $\phi OCH_2 C(=O)-$ | Na |
| (16.) | $\phi OCH_2 C(=O)-$ | H |
| (17.) | thienyl-$CH_2C(=O)-$ | H |
| (18.) | thienyl-$CH_2C(=O)-$ | H |
| (19.) | $NCCH_2 C(=O)-$ | H |
| (20.) | $CF_3 SCH_2 C(=O)-$ | H |
| (21.) | $\phi CH(NH_2)C(=O)-$ | H |

-continued

| Compound | $R^1$ | $R^4$ |
|---|---|---|
| (22.) | $\phi CH_2 C(=O)-$ | Na |
| (23.) | $\phi OCH_2 C(=O)-$ | Na |
| (24.) | $CF_3 SCH_2 C(=O)-$ | Na |
| (25.) | thienyl-$CH_2C(=O)-$ | Na |
| (26.) | $\phi CH(NH_2)C(=O)-$ | H |

EXAMPLE 19

Preparation of Pharmaceutical Compositions

One such unit dosage form consists of 3-(2-aminoethylthio)-6-phenylacetamido-7-oxo-1-azabicyclo[3.2.0-]hept-2-ene-2-carboxylic acid with 20 mg of lactose and 5 mg of magnesium stearate and placing the 145 mg mixture into a No. 3 gelatin capsule. Similarly, by employing more of the active ingredient and less lactose, other dosage forms can be put up in No. 3 gelatin capsules and should it be necessary to mix more than 145 mg of ingredients together, larger capsules such as compressed tablets and pills can also be prepared. The following examples are illustrative of the preparation of pharmaceutical formulations:

| TABLET | PER TABLET |
|---|---|
| 3-(2-aminoethylthio)-6-phenyl-acetamido-7-oxo-1-azabicyclo-[3.2.0]hept-2-ene-2-carboxylic acid | 125 mg |
| Cornstarch, U.S.P. | 6 mg |
| Dicalcium Phosphate | 192 mg |
| Lactose, U.S.P. | 190 mg |
| Magnesium Stearate | Balance/800 mg |

The active ingredient is blended with the dicalcium phosphate, lactose and about half of the cornstarch. The mixture is then granulated with 15% cornstarch paste (6 mg) and rough-screened. It is dried at 45° C. and screened again through No. 16 screens. The balance of the cornstarch and magnesium stearate is added and the mixture is compressed into tablets, approximately 0.5 inch in diameter each weighing 800 mg.

| PARENTERAL SOLUTION | PER TABLET |
|---|---|
| Ampoule: | |
| 3-(2-aminoethylthio)-6-phenyl-acetamido-7-oxo-1-azabicyclo-[3.2.0]hept-2-ene-2-carboxylic acid | 500 mg |
| Diluent: Sterile Water for Injection | 2 cc |

| | PER TABLET |
|---|---|
| OPTHALMIC SOLUTION | |
| 3-(2-aminoethylthio)-6-phenyl-acetamido-7-oxo-1-azabicyclo-[3.2.0]hept-2-ene-2-carboxylic acid | 100 mg |
| Hydrocypropylmethyl Cellulose | 5 mg |
| Sterile Water to | 1 ml |
| OPTIC SOLUTION | |
| 3-(2-aminoethylthio)-6-phenyl-acetamido-7-oxo-1-azabicyclo-[3.2.0]hept-2-ene-2-carboxylic acid | 100 mg |
| Benzalkonium Chloride | 0.1 mg |
| Sterile Water to | 1 ml |
| TOPICAL OINTMENT | |
| 3-(2-aminoethylthio)-6-phenyl-acetamido-7-oxo-1-azabicyclo-[3.2.0]hept-2-ene-2-carboxylic acid | 100 mg |
| Polyethylene Glycol 4000 U.S.P. | 400 mg |
| Polyethylene Glycol 400 U.S.P. | 1.0 gram |

The active ingredient in the above formulations may be administered alone or in combination with other biologically active ingredients as, for example, with other antibacterial agents such as lincomycin, a penicillin, streptomycin, novobiocin, gentamicin, neomycin, colistin and kanamycin, or with other therapeutic agents such as probenecid.

What is claimed is:

1. An antibiotic pharmaceutical composition comprising a therapeutically effective amount of a compound and a pharmaceutical carrier therefor.

2. A compound having the structure:

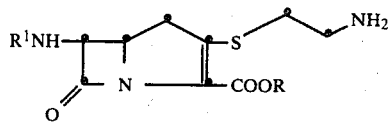

wherein R is hydrogen, the pharmaceutically acceptable salts or cations or lower alkyl having 1-4 carbon atoms; lower alkenyl having 1-4 carbon atoms; benzyl, p-nitrobenzyl, pivaloyloxymethyl, 3-phthalidyl or phenacyl;

and $R^1$ is 2-furylacetyl, 5-nitrofurylacetyl, 3-furylacetyl, 2-thienylacetyl, 5-chlorothienylacetyl, 5-methoxythienylacetyl, α-guanidino-2-thienylacetyl, 3-thienylacetyl, 4-methylthienylacetyl, 3-isothiazolylacetyl, 4-methoxyisothiazolylacetyl, 4-isothiazolylacetyl, 3-methylisothiazolylacetyl, 5-isothiazolylacetyl, 3-chloroisothiazolylacetyl, 3-methyl-1,2,5-oxadiazolylacetyl, 1,2,5-thiadiazolyl-4-acetyl, 3-methyl-1,2,5-thiadiazolyl-4-acetyl, 3-chloro-1,2,5-thiadiazolyl-4-acetyl, 3-methoxy-1,2,5-thiadiazolyl-4-acetyl, 4-pyridylthioacetyl, cyanoacetyl, tetrazolylacetyl, 2-thienylglycyl, 3-thienylglycyl, 2-thienylmalonyl and 3-thienylmalonyl.

* * * * *

UNITED STATES PATENT AND TRADEMARK OFFICE
CERTIFICATE OF CORRECTION

PATENT NO. : 4,281,002

DATED : July 28, 1981

INVENTOR(S) : Burton G. Christensen et al

It is certified that error appears in the above—identified patent and that said Letters Patent is hereby corrected as shown below:

In Claim 1, Col. 38, delete "1." and insert therefor -- 2. --; also insert the words -- according to Claim 1 -- after "compound" and before "and".

In Claim 2, Col. 38, delete "2." and insert therefor -- 1. --.

Signed and Sealed this

Twenty-fourth Day of November 1981

[SEAL]

Attest:

GERALD J. MOSSINGHOFF

Attesting Officer

Commissioner of Patents and Trademarks